United States Patent
Prisinzano et al.

(10) Patent No.: US 7,728,001 B2
(45) Date of Patent: Jun. 1, 2010

(54) OPIOID RECEPTOR LIGANDS AND METHODS FOR THEIR PREPARATION

(75) Inventors: Thomas Prisinzano, Iowa City, IA (US); Richard Brian Rothman, Ellicott City, MD (US)

(73) Assignee: University of Iowa Research Foundation, Iowa City, IA (US)

( * ) Notice: Subject to any disclaimer, the term of this patent is extended or adjusted under 35 U.S.C. 154(b) by 1075 days.

(21) Appl. No.: 11/224,706

(22) Filed: Sep. 12, 2005

(65) Prior Publication Data
US 2006/0058264 A1    Mar. 16, 2006

Related U.S. Application Data

(60) Provisional application No. 60/608,627, filed on Sep. 10, 2004, provisional application No. 60/667,238, filed on Apr. 1, 2005.

(51) Int. Cl.
*A61K 31/38* (2006.01)
*C07D 335/08* (2006.01)
*C07D 311/78* (2006.01)

(52) U.S. Cl. ............ 514/297; 514/437; 514/454; 514/455; 546/101; 549/26; 549/27; 549/280

(58) Field of Classification Search ............ 549/26, 549/27, 280; 546/101; 514/297, 437, 454, 514/455
See application file for complete search history.

(56) References Cited

FOREIGN PATENT DOCUMENTS
WO    WO 2005/089745    9/2005

OTHER PUBLICATIONS

Beguin, Cecile et al., "Synthesis and in vitro pharmacological evaluation of salvinorin A analogues modified at C(2)", *Bioorganic & Medicinal Chemistry Letters*, vol. 15, 2761-2765 (2005).

Brinner, Kristin M. et al., "Potent 4-aminopiperidine based antimalarial agents", *Bioorganic & Medicinal Chemistry Letters*, vol. 15, 345-348, (2005).

Chavkin, Charles et al., "Salvinorin A, an Active Component of the Hallucinogenic Sage *Salvia divinorum* is a Highly efficacious k-Opioid Receptor Agonist: Structural and Functional Considerations", *The Journal of Pharmacology and Experimental Therapeutics*, vol. 308, 1197-1203, (2004).

Harding, Wayne W. et al., "Neoclerodane Diterpenes as a Novel Scaffold for u Opioid Receptor.Ligands", *J. Med. Chem.*, vol. 48, 4765-4771 (2005).

Harding, Wayne W. et al., "Salvinicins A and B, New Neoclerodane Diterpenes from *Salvia divinorum*", *Org. Lett.*, vol. 7, No. 14, 3017-3020, (2005).

(Continued)

*Primary Examiner*—Janet L. Andres
*Assistant Examiner*—Raymond Covington
(74) *Attorney, Agent, or Firm*—Viksnins Harris & Padys PLLP

(57) ABSTRACT

The invention provides novel compounds of formula I:

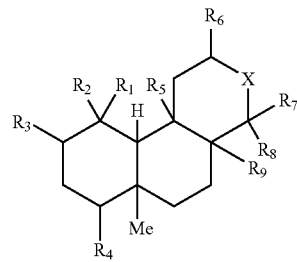

that are opioid receptor ligands. The invention also provides pharmaceutical compositions comprising such compounds as well as methods for treating diseases associated with opioid receptor function by administering such compounds to a mammal in need of treatment. The invention also provides an improved method for isolating intermediate materials useful for obtaining compounds of formula I.

19 Claims, 11 Drawing Sheets

OTHER PUBLICATIONS

Koreeda, Masato et al., "The Absolute Stereochemistry of Salvinorins", *Chemistry Letters*, 2015-2018, (1990).

Lee, David Y. W. et al., "Synthesis and in vitro pharmacological studies of new C(2) modified salvinorin A analogues", *Bioorganic & Medicinal Chemistry Letters*, vol. 15, 3744-3747, (2005).

Sarma, A. S. et al., "Proton and carbon-13NMR studies of trans-cletrodane diterpenoids and congerers: stereochemical implications and certain correlations with cis-clerodanes", Indian Journal of Chemistry, Abstract, (1985).

Tidgewell, Kevin et al., A facile method for the preparation of deuterium labeled salvinorin A: synthesis of [ $2,2,2-^2H_3$ ]-salvinorin A, Biorganic & Medicinal Chemistry Letters, vol. 14, 5099-5102, (2004).

Valdes, Leander J. III et al., "Salvinorin C, a New Neoclerodane Diterpene from a Bioactive Fraction of the Hallucinogenic Mexican Mint *Salvia divinorum*", *Organic Letters*, vol. 3, No. 24, 3935-3937, (2001).

Valdes, Leander J. III et al. Divinorin A, a Psychotropic Terpenoid, and Divinorin B from the Hallucinogenic Mexican Mint *Salvia divinorum*, *J. Org. Chem.*, vol. 49, 4716-4721, 1984.

Munro, Thomas A., et al., Studies toward the Pharmacophore of Salvinorin A, a Potent k Opioid Receptor Agonist, *J. Med. Chem.*, vol. 48, 345-348, 2005.

PCT International Search Report, PCT/US2005/032505.

Tidgewell, Kevin, "Herkinorin Analogues with Differential β-Arrestin-2 Interactions", *J. Med. Chem.*, vol. 51, 2421-2431 (2008).

Butelman, Eduardo R, "The effects of herkinorin, the first μ-selective ligand from salvinorin A-derived scaffold, in a neuroendocrine biomarker assay in non-human primates", *Journal of Pharmacology and Experimental Therapeutics*, 1-25, (Jul. 1, 2008).

Tidgewell, Kevin, "Synthesis of Salvinorin A analogues as optoid receptor probes", *J. Nat. Prod. 69*, 914-918 (2006).

Reagents and conditions: (a) Na$_2$CO$_3$, MeOH; (b) Appropriate alkyl acid chloride, DMAP, CH$_2$Cl$_2$; (c) Appropriate benzoyl chloride, DMAP, CH$_2$Cl$_2$; (d) Appropriate sulfonyl chloride, DMAP, CH$_2$Cl$_2$

OPIOID RECEPTOR LIGANDS AND METHODS FOR THEIR PREPARATION

RELATED APPLICATION

This application claims the benefit of priority of U.S. application Ser. No. 60/608,627 filed Sep. 10, 2004 and U.S. application Ser. No. 60/667,238 filed Apr. 1, 2005, which applications are herein incorporated by reference.

BACKGROUND OF THE INVENTION

The opium poppy, Papaver somniferum, has been used for centuries for the relief of pain and to induce sleep (Casy, A. F.; Parfitt, R. T. Opioid analgesics: chemistry and receptors; Plenum Press: New York, 1986; xv, 518). Among the most important constituents in opium are the alkaloids morphine and codeine. Many of the agonists and antagonists derived from these alkaloids are essential for the practice of modern medicine. While many potent agonists are effective analgesics, they have undesirable side effects, such as tolerance, dependence, and respiratory depression. (Stein, C.; Schafer, M.; Machelska, H. *Nat. Med.* 2003, 9, 1003-1008).

Endogenous opioid peptides are known and are involved in the mediation or modulation of a variety of mammalian physiological processes, many of which are mimicked by opiates or other non-endogenous opioid ligands. Some of the processes that have been suggested include analgesia, tolerance and dependence, appetite, renal function, gastrointestinal motility, gastric secretion, respiratory depression, learning and memory, mental illness, epileptic seizures and other neurological disorders and cardiovascular responses.

Intensive research of the last two decades has given us a better understanding of opioid receptor structure, distribution, and pharmacology (Waldhoer, M.; Bartlett, S. E.; Whistler, J. L. *Annu. Rev. Biochem.* 2004, 73, 953-990). Three types of opioid receptors known as mu ($\mu$), delta, ($\delta$), and kappa ($\kappa$) and receptor subtypes have been identified, and the mRNA encoding these receptors has been isolated. There is substantial pharmacological evidence for subtypes of each (Reisine, T. Neurotransmitter Receptors V: Opiate Receptors. *Neuropharmacology* 1995, 34, 463-472) It has become clear that each receptor mediates unique pharmacological responses and is differentially distributed in the central nervous system (Goldstein, A.; Naidu, A., *Mol. Pharmacol.* 1989, 36, 265-272; and Mansour, A.; Fox, C. A.; Akil, H.; Watson, S. J., *Trends Neurosci.* 1995, 18, 22-29).

The endogenous ligands for the opioid receptors are neuropeptides (Casy, A. F.; Parfitt, R. T. Opioid analgesics: chemistry and receptors; Plenum Press: New York, 1986; xv, 518). To date, three families of endogenous opioid peptides have been identified. They are classified, β-endorphins, enkephalins, and dynorphins (Gutstein, H.; Akil, H. Opioid Analgesics. Goodman & Gilman's The Pharmacological Basis of Therapeutics; 10th ed.; McGraw-Hill: New York, 2001; pp 569-619; and Eguchi, M., *Med. Res. Rev.* 2004, 24, 182-212). Although most of these endogenous opioids have little selectivity for opioid receptors, it is generally accepted that β-endorphins, enkephalins, and dynorphins display greater affinity for $\mu$, $\delta$ and $\kappa$ receptors respectively.

There are several structural classes of nonpeptidic opioid receptor ligands (Eguchi, M., *Med. Res. Rev.* 2004, 24, 182-212; Kaczor, A.; Matosiuk, D., *Curr. Med. Chem.* 2002, 9, 1567-1589; and Kaczor, A.; Matosiuk, D., *Curr. Med. Chem.*, 2002, 9, 1591-1603). The oldest class of compounds are those derived from morphine (2) (FIG. 1). Examples of other structural classes include fentanyl (3), cyclazocine (4), SNC 80 (5), U50,488H (6), and 3FLB (7) (see FIG. 1). The common structural motif in all of these ligands is the presence of a basic amino group.

Salvinorin A is a unique opioid receptor ligand (1, FIG. 1). It bears little structural similarity to other structural classes of nonpeptidic opioid receptor ligands such as morphine, fentanyl, cyclazocine, SNC 80, U50,488H, and 3FLB, which all possess a basic amino group. Until recently it has been assumed that the presence of a positively charged nitrogen atom in opioid compounds represented an absolute requirement for their interaction with opioid receptors (Rees, D. C.; Hunter, J. C. Comprehensive Medicinal Chemistry; Pergammon: New York, 1990; pp 805-846). The general assumption was that this cationic amino charge on the opioid ligand would interact with the side chain carboxyl group of an aspartate residue located in TM III of the opioid receptor (Eguchi, M., *Med. Res. Rev.* 2004, 24, 182-212; Surratt, C.; Johnson, P.; Moriwaki, A.; Seidleck, B.; Blaschak, C. et al. *J. Biol. Chem.* 1994, 269, 20548-20553; and Lu, Y.; Weltrowska, G.; Lemieux, C.; Chung, N. N.; Schiller, P. W., *Bioorg. Med. Chem. Lett.*, 2001, 11, 323-325). Given the structure and potency of salvinorin A (1), this interaction is unlikely.

Salvinorin A, originally isolated from the leaves of *Salvia divinorum*, was found to be very selective for $\kappa$ receptors over $\mu$ and $\delta$ opioid receptors, as well as over a battery of other receptors. This was the first report of a nonnitrogenous $\kappa$ opioid receptor agonist (Ortega, A.; Blount, J. F.; Manchand, P. S. Salvinorin, *J. Chem. Soc. Perkin Trans.* 1, 1982, 2505-2508; Valdes III, L. J.; Butler, W. M.; Hatfield, G. M.; Paul, A. G.; Koreeda, M. Divinorin A, *J. Org. Chem.* 1984, 49, 4716-4720; and Roth, B. L.; Baner, K.; Westkaemper, R.; Siebert, D.; Rice, K. C. et al., *Proc. Natl. Acad. Sci. USA* 2002, 99, 11934-11939).

*Salvia divinorum* is a plant from the Sage family that has been used in the traditional spiritual practices by the Mazatec Indians of Oaxaca, Mexico to produce "mystical" or hallucinogenic experiences (Valdes III, L. J.; Diaz, J. L.; Paul, A. G., *J. Ethnopharmacol.* 1983, 7, 287-312). The plant has become widely available through the internet and its recreational use by young adults and adolescents is increasing. Recipes for leaf extracts, elixirs and tinctures are easily found on the internet. Due to the recent increase in the popularity of this plant, the DEA has recently placed it on the list of drugs of concern (Center, N. D. I. *Salvia divinorum*. In Information Bulletin; U.S. Department of Justice: Johnstown, Pa., 2003; and Giroud, C.; Felber, F.; Augsburger, M.; Horisberger, B.; Rivier, L. et al., *Forensic Sci. Int.* 2000, 112, 143-150).

Currently, *Salvia divinorum* is unregulated in most countries and it is available throughout the world over the internet. It is listed as a controlled substance in Denmark, Australia, and Italy. At present, U.S. laws for controlled substances do not ban the use of *Salvia divinorum* or its active components. This has resulted in various on-line botanical companies advertising and selling *Salvia divinorum* as a legal alternative to other regulated plant hallucinogens.

As mentioned earlier, salvinorin A is a hallucinogen. A smoked dose of 200-500 µg produces profound hallucinations in humans (Valdes III, L. J.; Chang, H. M.; Visger, D. C.; Koreeda, M., *Org. Lett.* 2001, 3, 3935-3937). The potency of salvinorin A, therefore, is similar to the highly active synthetic hallucinogen LSD. However, unlike LSD and other classical hallucinogens, salvinorin A has no activity at the serotonin $5\text{-HT}_{2A}$ receptor, the presumed molecular target for these compounds (Glennon, R. A.; Titeler, M.; McKenney, J. D., *Life Sci.* 1984, 35, 2505-2511; Titeler, M.; Lyon, R. A.; Glennon, R. A., *Psychopharmacology* 1988, 94, 213-216; Egan, C. T.; Herrick-Davis, K.; Miller, K.; Glennon, R. A.;

Teitler, M., *Psychopharmacology* 1998, 136, 409-414; and Nichols, D. E. Hallucinogens. *Pharmacol. Ther.* 2004, 101, 131-181).

The pharmacology of salvinorin A appears to be different than other κ agonists (Wang,Y.; Tang, K.; Inan, S.; Siebert, D. J.; Holzgrabe, U; Lee, D. Y. W.; Huang, P.; Li, J. G.; Cowan, A.; Liu-Chen, L.-Y., *J. Pharmacol. Exp. Ther.* 2004, 312, 220-230).

Currently, there is a need for new opioid receptor ligands that have fewer side effects than known ligands. Such ligands would be useful for the treatment of diseases and conditions associated with the activity of opioid receptors. Such ligands would also be useful as pharmacological tools for the further study of the physiological processes associated with opioid receptor structure and function.

SUMMARY OF THE INVENTION

In one embodiment the invention provides novel opioid ligands. Accordingly, the invention provides a compound of the invention which is a compound of formula I:

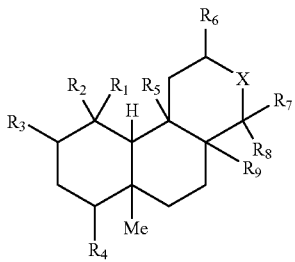

wherein:
- $R_1$ is H, hydroxy, ($C_1$-$C_6$)alkyl, ($C_1$-$C_6$)alkoxy, or ($C_1$-$C_6$)alkanoyloxy and $R_2$ is H or ($C_1$-$C_6$)alkyl; or $R_1$ and $R_2$ taken together are oxo (=O), thioxo (=S), or =$NR_a$;
- $R_3$ is H, halo, azido, hydroxy, ($C_1$-$C_6$)alkyl, ($C_1$-$C_6$)alkoxy, ($C_1$-$C_6$)alkylthio, ($C_1$-$C_6$)alkoxy($C_1$-$C_6$)alkoxy, aryl, heteroaryl, aryloxy, heteroaryloxy, aryl($C_1$-$C_6$)alkyl, aryl($C_1$-$C_6$)alkoxy, heteroaryl($C_1$-$C_6$)alkyl, heteroaryl($C_1$-$C_6$)alkoxy, Het, Het($C_1$-$C_6$)alkyl, Het($C_1$-$C_6$)alkoxy, formyloxy, acetoxy, $R_cC$(=O)O—, $R_cC$(=S)O—, $R_cC$(=O)S—, ($R_g$)$_3$SiO—, $R_dR_eNC$(=O)O—, ($R_h$)$_3$C(=$NR_d$)O—, $R_mR_nN$—, or $R_bS$(=O)$_2$O—;
- $R_4$ is H, hydroxymethyl, ($C_1$-$C_6$)alkyl, ($C_1$-$C_6$)alkoxymethyl, carboxy, ($C_1$-$C_6$)alkoxycarbonyl or $R_dR_eNC$(=O)—;
- $R_5$ is H or ($C_1$-$C_6$)alkyl;
- $R_6$ is ($C_1$-$C_6$)alkyl, ($C_1$-$C_6$)cycloalkyl, aryl, Het, carboxy, $R_jR_kNC$(=O)—, or heteroaryl;
- $R_7$ and $R_8$ taken together are oxo (=O), thioxo (=S), or =$NR_a$;
- $R_9$ is H or ($C_1$-$C_6$)alkyl;
- X is —O—, —S—, or —$NR_a$—;
- each $R_a$ is independently H, ($C_1$-$C_6$)alkyl, aryl, heteroaryl, aryl($C_1$-$C_6$)alkyl, or heteroaryl($C_1$-$C_6$)alkyl;
- each $R_b$ is independently H, ($C_1$-$C_6$)alkyl, ($C_2$-$C_6$)alkenyl, aryl, heteroaryl, aryl($C_1$-$C_6$)alkyl, Het, Het($C_1$-$C_6$)alkyl, or heteroaryl($C_1$-$C_6$)alkyl;
- each $R_c$ is independently H, ($C_2$-$C_6$)alkyl, ($C_2$-$C_6$)alkenyl, ($C_2$-$C_6$)alkoxycarbonyl, aryl, heteroaryl, aryl($C_1$-$C_6$)alkyl, Het, Het($C_1$-$C_6$)alkyl, or heteroaryl($C_1$-$C_6$)alkyl;
- each $R_d$ and $R_e$ is independently H, ($C_1$-$C_6$)alkyl, ($C_1$-$C_6$)alkenyl, aryl, heteroaryl, aryl($C_1$-$C_6$)alkyl, or heteroaryl($C_1$-$C_6$)alkyl;
- each $R_g$ is independently ($C_1$-$C_6$)alkyl;
- each $R_h$ is independently H, ($C_1$-$C_6$)alkyl, fluoro, or chloro;
- each $R_j$ and $R_k$ is independently H, ($C_1$-$C_6$)alkyl, ($C_1$-$C_6$)alkenyl, aryl, heteroaryl, aryl($C_1$-$C_6$)alkyl, Het, Het($C_1$-$C_6$)alkyl, or heteroaryl($C_1$-$C_6$)alkyl;
- each $R_m$ and $R_n$ is independently H, ($C_1$-$C_6$)alkyl, ($C_1$-$C_6$)alkenyl, aryl, heteroaryl, aryloxy, heteroaryloxy, aryl($C_1$-$C_6$)alkyl, aryl($C_1$-$C_6$)alkoxy, heteroaryl($C_1$-$C_6$)alkyl, heteroaryl($C_1$-$C_6$)alkoxy, Het, Het($C_1$-$C_6$)alkyl, Het($C_1$-$C_6$)alkoxy, ($C_1$-$C_6$)alkanoyloxy, $R_pC$(=O)—, $R_dR_eNC$(=O)—, ($R_h$)$_3$C(=$NR_d$)—, or $R_bS$(=O)$_2$—;
- each $R_p$ is independently H, ($C_1$-$C_6$)alkyl, ($C_2$-$C_6$)alkenyl, aryl, heteroaryl, aryl($C_1$-$C_6$)alkyl, Het, Het($C_1$-$C_6$)alkyl, or heteroaryl($C_1$-$C_6$)alkyl; and
- each $R_q$ is independently H, ($C_1$-$C_6$)alkyl, ($C_2$-$C_6$)alkenyl, aryl, heteroaryl, aryl($C_1$-$C_6$)alkyl, or heteroaryl($C_1$-$C_6$)alkyl;
- wherein any aryl or heteroaryl of $R_3$, $R_6$, and $R_a$-$R_e$, and $R_j$-$R_q$ is optionally substituted with one or more (e.g. 1, 2, 3, or 4) halo, hydroxy, ($C_1$-$C_6$)alkyl, ($C_1$-$C_6$)alkoxy, ($C_1$-$C_6$)alkanoyloxy, ($C_1$-$C_6$)alkoxycarbonyl, cyano, nitro, trifluomethyl, trifluoromethoxy, $R_tS$(=O)$_2$—, or $R_uR_vN$; wherein $R_u$ and $R_v$ are each independently H or ($C_1$-$C_6$)alkyl;
- each $R_t$ is independently H, ($C_1$-$C_6$)alkyl, ($C_2$-$C_6$)alkenyl, aryl, heteroaryl, aryl($C_1$-$C_6$)alkyl, Het, Het($C_1$-$C_6$)alkyl, or heteroaryl($C_1$-$C_6$)alkyl;
- wherein any aryl or heteroaryl of $R_t$ is optionally substituted with one or more (e.g. 1, 2, 3, or 4) halo, hydroxy, ($C_1$-$C_6$)alkyl, ($C_1$-$C_6$)alkoxy, ($C_1$-$C_6$)alkanoyloxy, ($C_1$-$C_6$)alkoxycarbonyl, cyano, nitro, trifluomethyl, trifluoromethoxy, or $R_uR_vN$; wherein $R_u$ and $R_v$ are each independently H or ($C_1$-$C_6$)alkyl; and
- wherein any Het of $R_3$, $R_6$, $R_b$, $R_c$, and $R_j$-$R_q$ is optionally substituted with one or more (e.g. 1, 2, 3, or 4) halo, hydroxy, ($C_1$-$C_6$)alkyl, ($C_1$-$C_6$)alkoxy, ($C_1$-$C_6$)alkanoyloxy, ($C_1$-$C_6$)alkoxycarbonyl, cyano, nitro, trifluomethyl, trifluoromethoxy, oxo (=O), thioxo (=S), $R_qS$(=O)$_2$O—, aryl, heteroaryl, or $R_uR_vN$; wherein $R_u$ and $R_v$ are each independently H or ($C_1$-$C_6$)alkyl;
- or a pharmaceutically acceptable salt thereof;
- provided that $R_3$ is not acetoxy, when $R_1$ and $R_2$ taken together are oxo, $R_4$ is methoxycarbonyl, $R_5$ is methyl, $R_6$ is 2-furyl, $R_7$ and $R_8$ taken together are oxo (=O), $R_9$ is hydrogen, and X is —O—.

The invention also provides a pharmaceutical composition comprising a compound of formula I and a pharmaceutically acceptable diluent or carrier.

The invention also provides a method for modulating the activity of an opioid receptor comprising contacting the receptor (in vitro or in vivo) with an effective modulatory amount of a compound of formula I.

The invention also provides a therapeutic method for treating a disease or condition in a mammal wherein the activity of an opioid receptor is implicated and modulation of the action of the receptor is desired (e.g. pain, drug addiction, or alcohol addiction) comprising administering to the mammal, an effective amount of a compound of formula I.

The invention also provides a method for preparing a compound of formula (IV):

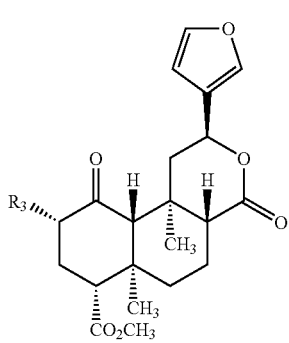

IV wherein $R_3$ is formyloxy, $R_cC(=O)O—$, or $R_bS(=O)_2O—$; comprising extracting *Salvia divinorum* leaves with a suitable organic solvent (e.g., acetone, $Et_2O$, $CH_2Cl_2$, $CHCl_3$, benzene, toluene, or a mixture thereof); removing the organic solvent (e.g. under reduced pressure) to provide a solid; partitioning the solid between hexanes and aqueous methanol and $Na_2CO_3$; removing the aqueous methanol under reduced pressure to provide an intermediate alcohol; and acylating the alcohol with the requisite acylating agent followed by column chromatography using a gradient of ethyl acetate/n-hexane to provide the compound of formula IV.

The invention also provides methods for isolating Salvinorin A from the leaves of *Salvia divinorum* plant. The extraction of the leaves of the *Salvia divinorum* plant yields Salvinorin A. The extraction step can be carried out in any suitable non-polar organic solvent. Suitable non-polar organic solvents include acetone, $Et_2O$, $CH_2Cl_2$, $CHCl_3$, benzene, and toluene or mixtures thereof.

The invention also provides a method for preparing a compound of formula (IV):

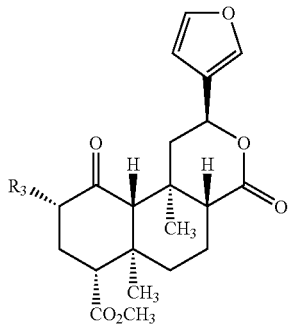

IV wherein $R_3$ is formyloxy, $R_cC(=O)O—$, or $R_bS(=O)_2O—$; comprising extracting *Salvia divinorum* leaves with acetone; removing the acetone to provide a solid; partitioning the solid between hexanes and aqueous methanol and $Na_2CO_3$; removing the aqueous methanol under reduced pressure to provide an intermediate alcohol; and acylating the alcohol with the requisite acylating agent to provide the compound of formula IV.

The invention also provides a method for preparing a compound of formula (IV):

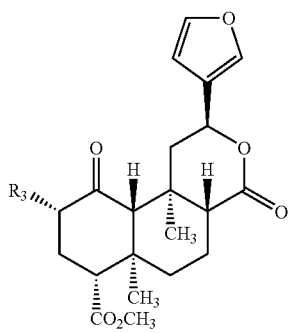

IV wherein $R_3$ is formyloxy, $R_cC(=O)O—$, or $R_bS(=O)_2O—$; comprising extracting *Salvia divinorum* leaves with a suitable organic solvent; removing the organic solvent to provide a solid; partitioning the solid between hexanes, aqueous methanol, and $Na_2CO_3$; removing the aqueous methanol under reduced pressure to provide an intermediate alcohol; acylating the alcohol with the requisite acylating agent to provide the compound of formula IV; and purifying the compound of formula IV by column chromatography on silica gel using an eluent gradient of increasing amounts of ethyl acetate in hexanes.

The invention also provides a method for obtaining a material comprising a compound of formula (IV)

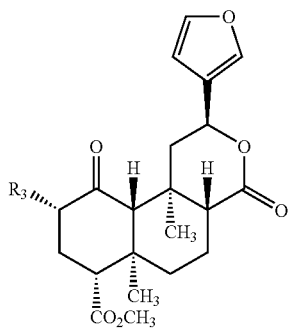

IV wherein $R_3$ is acyloxy; comprising extracting *Salvia divinorum* leaves with acetone; removing the acetone to provide a resulting material; and purifying the resulting material by column chromatography on silica gel to provide the material comprising a compound of formula (IV).

The invention also provides a compound of the invention (e.g. a compound of formula I or a salt thereof) for use in medical therapy.

The invention also provides the use of a compound of the invention to prepare a medicament useful for the treatment of a disease or condition in a mammal wherein the activity of an opioid receptor is implicated and modulation of the action of the receptor is desired.

The invention also provides a method for binding a compound of the invention to mammalian tissue comprising opioid receptors, in vivo or in vitro, comprising contacting the tissue with an amount of a compound of the invention effective to bind to said receptors. Tissue comprising a compound of the invention bound to opioid receptor sites can be used to measure the selectivity of test compounds for specific receptor subtypes, or can be used as a tool to identify potential therapeutic agents for the treatment of diseases or conditions associated with opioid receptor activity, by contacting said agents with said ligand-receptor complexes, and measuring the extent of displacement of the ligand and/or binding of the agent.

The invention also provides a detectably labeled (e.g. a radiolabeled) compound comprising a compound of formula I; or a pharmaceutically acceptable salt thereof, that comprises or is linked to one or more detectable groups.

The invention also provides processes and intermediates disclosed herein that are useful for preparing compounds of formula (I) or salts thereof. Certain compounds of formula (I) are useful as intermediates for preparing other compounds of formula (I).

DETAILED DESCRIPTION

Figure 1:
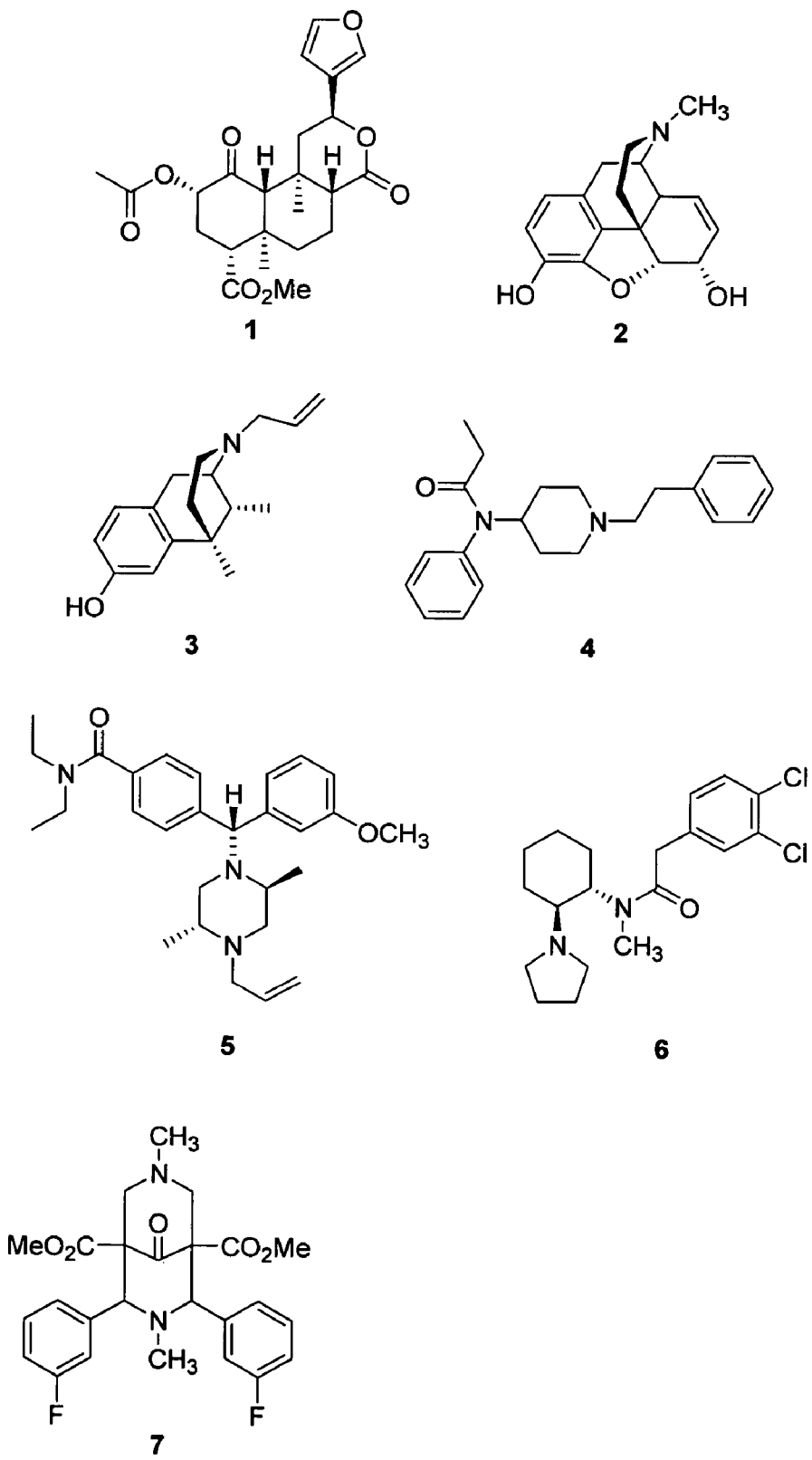
FIG. 1 Shows the structures of morphine (2), fentanyl (3), cyclazocine (4), SNC 80 (5), U50,488H (6), and 3FLB (7).

The following definitions are used, unless otherwise described: halo is fluoro, chloro, bromo, or iodo. Alkyl, alkoxy, etc. denote both straight and branched groups; but reference to an individual radical such as Apropyl@ embraces only the straight chain radical, a branched chain isomer such as Aisopropyl@ being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(Y) wherein Y is absent or is H, O, ($C_1$-$C_4$)alkyl, phenyl or benzyl, as well as a radical of an ortho-fused bicyclic heterocycle of about eight to ten ring atoms derived there from, particularly a benz-derivative or one derived by fusing a propylene, trimethylene, or tetramethylene diradical thereto. "Het" includes a mono or bicyclic saturated or partially unsaturated ring system comprising about 4 to about 12 atoms selected from carbon, O, S, and N. Examples of "Het" include dihydrofuran, tetrahydrofuran, pyrazoline, piperidine, morpholine, thiomorpholine, piperazine, indoline, isoindoline, pyrazolidine, imidazoline, imidazolidine, pyroline, pyrrolidine, chroman, and isochroman.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine opioid receptor binding and modulatory activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_1$-$C_6$)alkanoyl can be acetyl, propanoyl or butanoyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_2$-$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is hydroxy, ($C_1$-$C_6$)alkoxy, or ($C_1$-$C_6$)alkanoyloxy, and for $R_2$ is H.

A specific value for $R_1$ and $R_2$ taken together is oxo (=O), thioxo (=S), or =$NR_a$.

A specific value for $R_1$ and $R_2$ taken together is oxo (=O).

A specific value for $R_3$ is H, hydroxy, ($C_1$-$C_6$)alkyl, ($C_1$-$C_6$)alkoxy, aryl, heteroaryl, aryloxy, heteroaryloxy, aryl($C_1$-$C_6$)alkyl, aryl($C_1$-$C_6$)alkoxy, heteroaryl($C_1$-$C_6$)alkyl, heteroaryl($C_1$-$C_6$)alkoxy, formyloxy, $R_cC(=O)O$—, $(R_g)_3SiO$—, $R_dR_eNC(=O)O$—, $(R_h)_3C(=NR_d)O$—, or $R_bS(=O)_2O$—.

A specific value for $R_3$ is hydroxy, ($C_1$-$C_6$)alkoxy, aryloxy, heteroaryloxy, aryl($C_1$-$C_6$)alkoxy, heteroaryl($C_1$-$C_6$)alkoxy, formyloxy, $R_cC(=O)O$—, or $R_bS(=O)_2O$—.

A specific value for $R_3$ is formyloxy, $R_cC(=O)O$—, or $R_bS(=O)_2O$—.

A specific value for $R_3$ is propanoyloxy, isobutanoyloxy, methacryloyloxy, methoxyoxalyloxy, benzoyloxy, trimethylsilyloxy, imidazole-1-ylthiocarbonyloxy, methoxymethoxy, aminocarbonyloxy, butanoyloxy, pentanoyloxy, 1-bromobenzoyloxy, 2-bromobenzoyloxy, 3-bromobenzoyloxy, 4-methoxybenzoyloxy, 4-nitrobenzoyloxy, phenylsulfonyloxy, 4-methylphenylsulfonyloxy, 4-methoxyphenylsulfonyloxy, 4-bromophenylsulfonyloxy, (3-pyridylcarbonyloxy, methylsulfonyloxy, hydroxy, 1-imino-2,2,2-trichloroethoxy, phenylaminocarbonyloxy, allylaminocarbonyloxy, 3,4-dichlorobenzoyloxy, bromo, azido, amino, acetylamino, phenylcarbonylamino, methylsulfonylamino, phenylsulfonylamino, or benzoyloxy.

A specific value for $R_3$ is propanoyloxy, isobutanoyloxy, methacryloyloxy, methoxyoxalyloxy, 3-pyridylcarbonyloxy, methylsulfonyloxy, hydroxy, 1-imino-2,2,2-trichloroethoxy, phenylaminocarbonyloxy, allylaminocarbonyloxy, or benzoyloxy A specific value for $R_3$ is propanoyloxy, methylsulfonyloxy, or benzoyloxy.

A specific value for $R_3$ is benzoyloxy, 3-pyridylcarbonyloxy, or phenylaminocarbonyloxy.

A specific value for $R_4$ is hydroxymethyl, ($C_1$-$C_6$)alkoxymethyl, carboxy, ($C_1$-$C_6$)alkoxycarbonyl, or $R_dR_eNC(=O)$—.

A specific value for $R_4$ is carboxy, ($C_1$-$C_6$)alkoxycarbonyl; or $R_dR_eNC(=O)$—.

A specific value for $R_4$ is methoxycarbonyl.

A specific value for $R_5$ is H or methyl.

A specific value for $R_5$ is methyl.

A specific value for $R_6$ is aryl or heteroaryl, optionally substituted with one or more (e.g. 1, 2, 3, or 4) halo, hydroxy, $(C_1\text{-}C_6)$alkyl, $(C_1\text{-}C_6)$alkoxy, $(C_1\text{-}C_6)$alkanoyloxy, $(C_1\text{-}C_6)$alkoxycarbonyl, cyano, nitro, trifluomethyl, trifluoromethoxy, or $R_eR_fN$.

A specific value for $R_6$ is phenyl, thienyl, furanyl, pyrrolyl, or pyridyl, optionally substituted with one or more (e.g. 1, 2, 3, or 4) halo, hydroxy, $(C_1\text{-}C_6)$alkyl, $(C_1\text{-}C_6)$alkoxy, $(C_1\text{-}C_6)$alkanoyloxy, $(C_1\text{-}C_6)$alkoxycarbonyl, cyano, nitro, trifluomethyl, trifluoromethoxy, or $R_eR_fN$.

A specific value for $R_6$ is phenyl, or Het, optionally substituted with one or more (e.g. 1, 2, 3, or 4) halo, hydroxy, $(C_1\text{-}C_6)$alkyl, $(C_1\text{-}C_6)$alkoxy, $(C_1\text{-}C_6)$alkanoyloxy, $(C_1\text{-}C_6)$alkoxycarbonyl, cyano, nitro, trifluomethyl, trifluoromethoxy, or $R_eR_fN$.

A specific value for $R_6$ is 3-furyl, 3,4-dihydroxy-2,5-dimethoxytetrahydrofuran-3-yl, 2,5-dihydro-2,5-dimethoxyfuran-3-yl, carboxy, 2,5-dihydro-5-bromo-2-oxofuran-3-yl, 2-bromofuran-3-yl, 2,5-dimethoxytetrahydrofuran-3-yl, 1-methylsulfonylpyrrol-3-yl, 1-phenylsulfonylpyrrol-3-yl, 1-(4-methoxyphenyl)sulfonylpyrrol-3-yl, 1-(4-nitrophenyl)sulfonylpyrrol-3-yl, 3-pyrrolyl, 4-methoxycarbonylthiazol-2-yl, 4-methocycarbonyloxazol-2-yl, thiazol-2-yl, or oxazol-2-yl.

A specific value for $R_6$ is 3-furyl.

A specific value for $R_7$ and $R_8$ taken together is oxo.

A specific value for $R_9$ is H or methyl.

A specific value for $R_9$ is methyl.

A specific value for $R_9$ is H.

A specific value for X is —O—.

A specific value for $R_a$ is H, methyl, ethyl, phenyl, thienyl, furanyl, pyrrolyl, pyridyl, benzyl, phenethyl, thienylmethyl, furanylmethyl, pyrrolylmethyl, or pyridylmethyl.

A specific value for $R_b$ is H, methyl, ethyl, phenyl, thienyl, furanyl, pyrrolyl, pyridyl, benzyl, phenethyl, thienylmethyl, furanylmethyl, pyrrolylmethyl, or pyridylmethyl.

A specific value for $R_c$ is H, ethyl, phenyl, thienyl, furanyl, pyrrolyl, pyridyl, benzyl, phenethyl, thienylmethyl, furanylmethyl, pyrrolylmethyl, or pyridylmethyl.

A specific value for $R_d$ and $R_e$ is independently H, methyl, ethyl, phenyl, thienyl, furanyl, pyrrolyl, pyridyl, benzyl, phenethyl, thienylmethyl, furanylmethyl, pyrrolylmethyl, or pyridylmethyl.

A specific compound of the invention is a compound of formula (II):

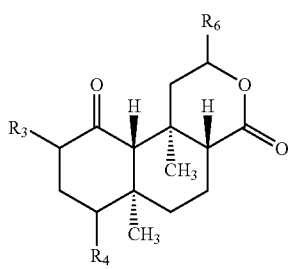

II or a pharmaceutically acceptable salt thereof; wherein $R_3$, $R_4$, and $R_6$ have any of the values, specific values or preferred values defined herein.

A specific compound of the invention is a compound of formula (III):

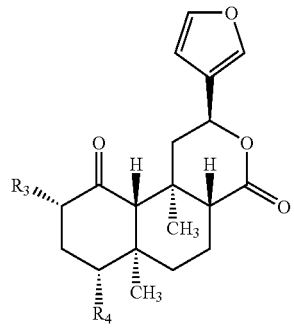

III or a pharmaceutically acceptable salt thereof; wherein $R_3$ and $R_4$ have any of the values, specific values or preferred values defined herein.

A specific compound of the invention is a compound of formula I:

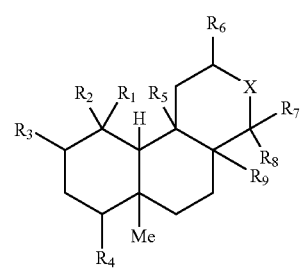

I wherein:
  $R_1$ is H, hydroxy, $(C_1\text{-}C_6)$alkyl, $(C_1\text{-}C_6)$alkoxy, or $(C_1\text{-}C_6)$alkanoyloxy and $R_2$ is H or $(C_1\text{-}C_6)$alkyl; or $R_1$ and $R_2$ taken together are oxo (=O), thioxo (=S), or =$NR_a$;
  $R_3$ is H, hydroxy, $(C_1\text{-}C_6)$alkyl, $(C_1\text{-}C_6)$alkoxy, aryl, heteroaryl, aryloxy, heteroaryloxy, aryl$(C_1\text{-}C_6)$alkyl, aryl$(C_1\text{-}C_6)$alkoxy, heteroaryl$(C_1\text{-}C_6)$alkyl, heteroaryl$(C_1\text{-}C_6)$alkoxy, formyloxy, $R_cC(=O)O—$, or $R_bS(=O)_2O—$;
  $R_4$ is H, hydroxymethyl, $(C_1\text{-}C_6)$alkyl, $(C_1\text{-}C_6)$alkoxymethyl, carboxy, $(C_1\text{-}C_6)$alkoxycarbonyl; or $R_dR_eNC(=O)—$;
  $R_5$ is H or $(C_1\text{-}C_6)$alkyl;
  $R_6$ is $(C_1\text{-}C_6)$alkyl, $(C_1\text{-}C_6)$cycloalkyl, aryl, or heteroaryl;
  $R_7$ and $R_8$ taken together are oxo (=O), thioxo (=S), or =$NR_a$;
  X is —O—, —S—, or —$NR_a$—;
  $R_9$ is hydrogen;
  each $R_a$ is independently H, $(C_1\text{-}C_6)$alkyl, aryl, heteroaryl, aryl$(C_1\text{-}C_6)$alkyl, or heteroaryl$(C_1\text{-}C_6)$alkyl;
  each $R_b$ is independently H, $(C_1\text{-}C_6)$alkyl, aryl, heteroaryl, aryl$(C_1\text{-}C_6)$alkyl, or heteroaryl$(C_1\text{-}C_6)$alkyl;
  each $R_c$ is independently H, $(C_2\text{-}C_6)$alkyl, aryl, heteroaryl, aryl$(C_1\text{-}C_6)$alkyl, or heteroaryl$(C_1\text{-}C_6)$alkyl;
  each $R_d$ and $R_e$ is independently H, $(C_1\text{-}C_6)$alkyl, aryl, heteroaryl, aryl$(C_1\text{-}C_6)$alkyl, or heteroaryl$(C_1\text{-}C_6)$alkyl;
  wherein any aryl or heteroaryl of $R_3$, $R_6$, or $R_a\text{-}R_e$ is optionally substituted with one or more (e.g. 1, 2, 3, or 4) halo, hydroxy, $(C_1\text{-}C_6)$alkyl, $(C_1\text{-}C_6)$alkoxy, $(C_1\text{-}C_6)$alkanoyloxy, $(C_1\text{-}C_6)$alkoxycarbonyl, cyano, nitro, trifluomethyl, trifluoromethoxy, or $R_eR_fN$; wherein $R_e$ and $R_f$ are each independently H or $(C_1-C_6)$alkyl;

or a pharmaceutically acceptable salt thereof.

In one specific embodiment the invention provides a pharmaceutical composition comprising a compound of formula I:

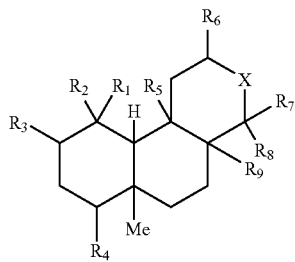

wherein:
- $R_1$ is H, hydroxy, $(C_1-C_6)$alkyl, $(C_1-C_6)$alkoxy, or $(C_1-C_6)$alkanoyloxy and $R_2$ is H or $(C_1-C_6)$alkyl; or $R_1$ and $R_2$ taken together are oxo (=O), thioxo (=S), or =$NR_a$;
- $R_3$ is H, hydroxy, $(C_1-C_6)$alkyl, $(C_1-C_6)$alkoxy, aryl, heteroaryl, aryloxy, heteroaryloxy, aryl$(C_1-C_6)$alkyl, aryl$(C_1-C_6)$alkoxy, heteroaryl$(C_1-C_6)$alkyl, heteroaryl$(C_1-C_6)$alkoxy, formyloxy, $R_cC(=O)O$—, or $R_bS(=O)_2O$—;
- $R_4$ is H, hydroxymethyl, $(C_1-C_6)$alkyl, $(C_1-C_6)$alkoxymethyl, carboxy, $(C_1-C_6)$alkoxycarbonyl; or $R_dR_eNC(=O)$—;
- $R_5$ is H or $(C_1-C_6)$alkyl;
- $R_6$ is $(C_1-C_6)$alkyl, $(C_1-C_6)$cycloalkyl, aryl, or heteroaryl;
- $R_7$ and $R_8$ taken together are oxo (=O), thioxo (=S), or =$NR_a$;
- $R_9$ is H or $(C_1-C_6)$alkyl;
- X is —O—, —S—, or —$NR_a$—;
- each $R_a$ is independently H, $(C_1-C_6)$alkyl, aryl, heteroaryl, aryl$(C_1-C_6)$alkyl, or heteroaryl$(C_1-C_6)$alkyl;
- each $R_b$ is independently H, $(C_1-C_6)$alkyl, aryl, heteroaryl, aryl$(C_1-C_6)$alkyl, or heteroaryl$(C_1-C_6)$alkyl;
- each $R_c$ is independently H, $(C_1-C_6)$alkyl, aryl, heteroaryl, aryl$(C_1-C_6)$alkyl, or heteroaryl$(C_1-C_6)$alkyl;
- each $R_d$ and $R_e$ is independently H, $(C_1-C_6)$alkyl, aryl, heteroaryl, aryl$(C_1-C_6)$alkyl, or heteroaryl$(C_1-C_6)$alkyl;

wherein any aryl or heteroaryl of $R_3$, $R_6$, or $R_a$-$R_e$ is optionally substituted with one or more (e.g. 1, 2, 3, or 4) halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluoromethyl, trifluoromethoxy, or $R_eR_fN$; wherein $R_e$ and $R_f$ are each independently H or $(C_1-C_6)$alkyl; or a pharmaceutically acceptable salt thereof; provided that the compound is not a compound of formula IV wherein $R_3$ acetoxy, propanoyloxy, or heptanoyloxy.

A specific group of compounds of the invention excludes a compound of formula IV wherein $R_3$ is 4-bromobenzoyloxy; a specific group of compounds of the invention excludes a compound of formula IV wherein $R_3$ is 1-naphthylcarbonyloxy; a specific group of compounds of the invention excludes a compound of formula IV wherein $R_3$ is heptanoyloxy; a specific group of compounds of the invention excludes a compound of formula IV wherein $R_3$ is pivaloyloxy; and/or a specific group of compounds of the invention excludes a compound of formula IV wherein $R_3$ is hydroxy; or a pharmaceutically acceptable salt thereof.

A specific compound of the invention is a compound of formula IV wherein $R_3$ is benzoyloxy; or a pharmaceutically acceptable salt thereof.

A specific compound of the invention is a compound of formula IV wherein $R_3$ is propanoyloxy; or a pharmaceutically acceptable salt thereof.

A specific compound of the invention is a compound of formula IV wherein $R_3$ is methylsulfonyloxy; or a pharmaceutically acceptable salt thereof.

A specific compound of the invention is a compound of formula IV wherein $R_3$ is aryl, heteroaryl, aryloxy, heteroaryloxy, aryl$(C_1-C_6)$alkyl, aryl$(C_1-C_6)$alkoxy, heteroaryl$(C_1-C_6)$alkyl, heteroaryl$(C_1-C_6)$alkoxy, $R_cC(=O)O$—, $R_dR_eNC(=O)O$—, or $R_bS(=O)_2O$—; each $R_b$ is independently aryl, heteroaryl, aryl$(C_1-C_6)$alkyl, or heteroaryl$(C_1-C_6)$alkyl; each $R_c$ is independently aryl, heteroaryl, aryl$(C_1-C_6)$alkyl, or heteroaryl$(C_1-C_6)$alkyl; $R_d$ is aryl, heteroaryl, aryl$(C_1-C_6)$alkyl, or heteroaryl$(C_1-C_6)$alkyl; and $R_e$ is independently H, $(C_1-C_6)$alkyl, $(C_1-C_6)$alkenyl, aryl, heteroaryl, aryl$(C_1-C_6)$alkyl, or heteroaryl$(C_1-C_6)$alkyl; wherein any aryl or heteroaryl of $R_3$, or $R_b$-$R_e$ is optionally substituted with one or more (e.g. 1, 2, 3, or 4) halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluoromethyl, trifluoromethoxy, or $R_eR_fN$; wherein $R_e$ and $R_f$ are each independently H or $(C_1-C_6)$alkyl; or a pharmaceutically acceptable salt thereof.

A specific compound of the invention is a compound of formula I:

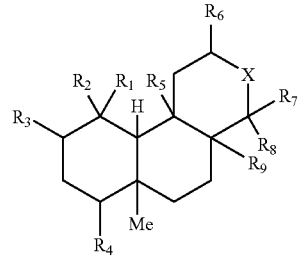

wherein:
- $R_1$ is H, hydroxy, $(C_1-C_6)$alkyl, $(C_1-C_6)$alkoxy, or $(C_1-C_6)$alkanoyloxy and $R_2$ is H or $(C_1-C_6)$alkyl; or $R_1$ and $R_2$ taken together are oxo (=O), thioxo (=S), or =$NR_a$;
- $R_3$ is H, hydroxy, $(C_1-C_6)$alkyl, $(C_1-C_6)$alkoxy, aryl, heteroaryl, aryloxy, heteroaryloxy, aryl$(C_1-C_6)$alkyl, aryl$(C_1-C_6)$alkoxy, heteroaryl$(C_1-C_6)$alkyl, heteroaryl$(C_1-C_6)$alkoxy, formyloxy, acetoxy, $R_cC(=O)O$—, $(R_g)_3SiO$—, $R_dR_eNC(=O)O$—, $(R_h)_3C(=NR_d)O$—, or $R_bS(=O)_2O$—;
- $R_4$ is H, hydroxymethyl, $(C_1-C_6)$alkyl, $(C_1-C_6)$alkoxymethyl, carboxy, $(C_1-C_6)$alkoxycarbonyl; or $R_dR_eNC(=O)$—;
- $R_5$ is H or $(C_1-C_6)$alkyl;
- $R_6$ is $(C_1-C_6)$alkyl, $(C_1-C_6)$cycloalkyl, aryl, or heteroaryl;
- $R_7$ and $R_8$ taken together are oxo (=O), thioxo (=S), or =$NR_a$;
- $R_9$ is H;
- X is —O—, —S—, or —$NR_a$—;
- each $R_a$ is independently H, $(C_1-C_6)$alkyl, aryl, heteroaryl, aryl$(C_1-C_6)$alkyl, or heteroaryl$(C_1-C_6)$alkyl;
- each $R_b$ is independently H, $(C_1-C_6)$alkyl, $(C_2-C_6)$alkenyl, aryl, heteroaryl, aryl$(C_1-C_6)$alkyl, or heteroaryl$(C_1-C_6)$alkyl;

each $R_c$ is independently H, $(C_2\text{-}C_6)$alkyl, $(C_2\text{-}C_6)$alkenyl, $(C_2\text{-}C_6)$alkoxycarbonyl, aryl, heteroaryl, aryl$(C_1\text{-}C_6)$alkyl, or heteroaryl$(C_1\text{-}C_6)$alkyl;

each $R_d$ and $R_e$ is independently H, $(C_1\text{-}C_6)$alkyl, $(C_1\text{-}C_6)$alkenyl, aryl, heteroaryl, aryl$(C_1\text{-}C_6)$alkyl, or heteroaryl $(C_1\text{-}C_6)$alkyl;

each $R_g$ is independently $(C_1\text{-}C_6)$alkyl; and each $R_h$ is independently H, $(C_1\text{-}C_6)$alkyl, fluoro, or chloro;

wherein any aryl or heteroaryl of $R_3$, $R_6$, or $R_a$-$R_e$ is optionally substituted with one or more (e.g. 1, 2, 3, or 4) halo, hydroxy, $(C_1\text{-}C_6)$alkyl, $(C_1\text{-}C_6)$alkoxy, $(C_1\text{-}C_6)$alkanoyloxy, $(C_1\text{-}C_6)$alkoxycarbonyl, cyano, nitro, trifluomethyl, trifluoromethoxy, or $R_eR_fN$; wherein $R_e$ and $R_f$ are each independently H or $(C_1\text{-}C_6)$alkyl;

or a pharmaceutically acceptable salt thereof;

provided that $R_3$ is not acetoxy, when $R_1$ and $R_2$ taken together are oxo, $R_4$ is methoxycarbonyl, $R_5$ is methyl, $R_6$ is 2-furyl, $R_7$ and $R_8$ taken together are oxo (=O), and X is —O—.

A specific intermediate that is useful for preparing other compounds of the invention is a compound of formula (I) or (II) wherein $R_6$ is carboxy.

A specific intermediate that is useful for preparing other compounds of the invention is a compound of formula (I), (II), (III), or (IV) wherein $R_3$ is halo, azido or amino.

Specific compounds of the invention also include compounds of formula I that comprise or that are linked to one or more detectable groups or isotopes. Such detectable compounds may be used as imaging agents or as probes for evaluating opioid receptor structure and function. For example, one or more detectable groups can be incorporated into the core of the compound, or can be attached to the compound directly, through a linking group, or through a chelating group. Suitable detectable groups include deuterium, tritium, iodine-125, iodine-131, iodine-123, astatine-210, carbon-11, carbon-14, nitrogen-13, or fluorine-18. Additionally, groups such as Tc-99m and Re-186 can be attached to a linking group or bound by a chelating group which is then attached to the compound of formula I directly or by means of a linker. Suitable radiolabeling techniques are routinely used in radiopharmaceutical chemistry.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

General Experimental and Data

Figure 2:
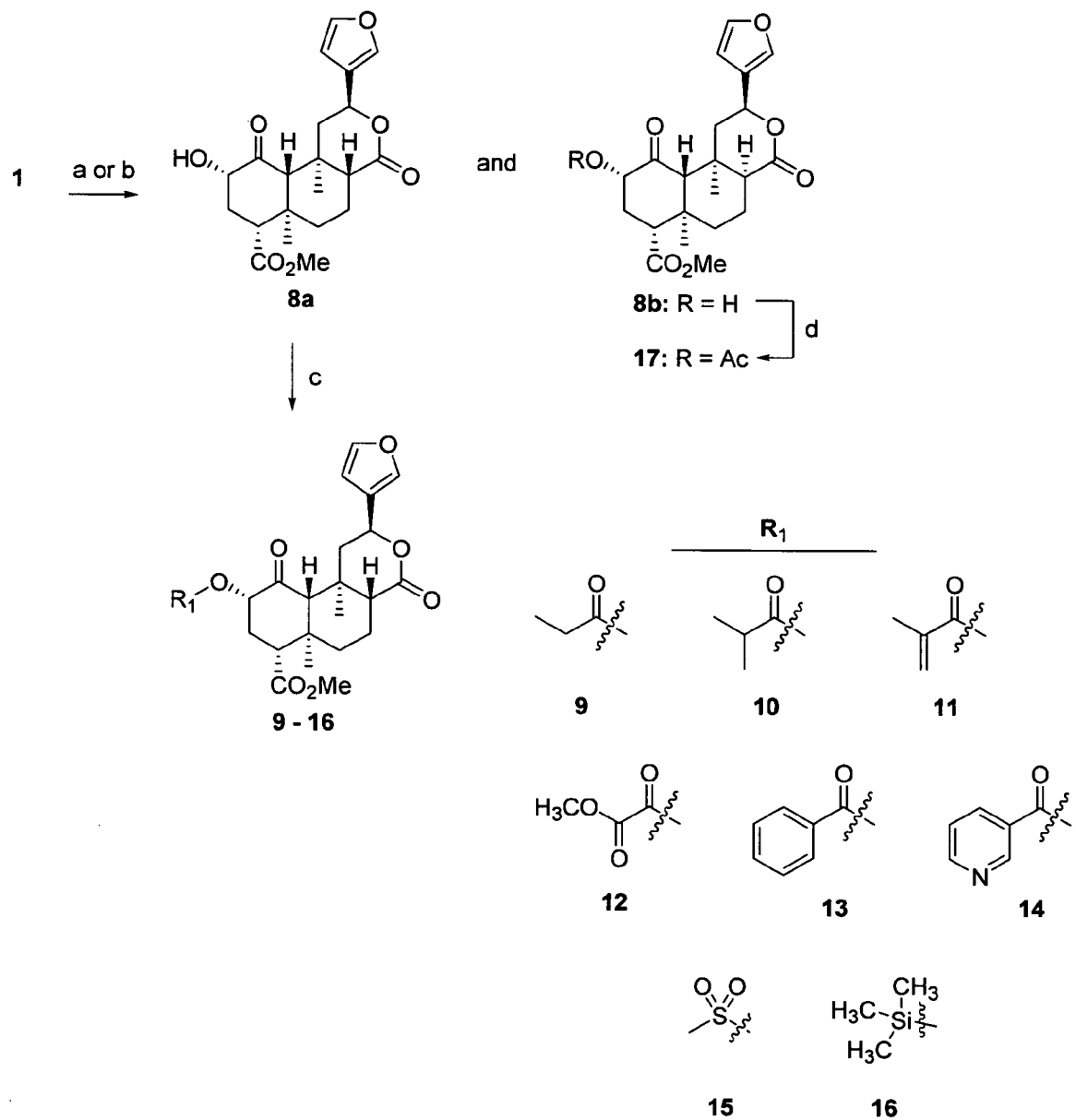
FIGS. 2-11 Illustrate the synthesis of representative compounds of the invention (9-68).

Rather than begin a lengthy total synthesis, efforts were initiated to isolate 1 from dried *Salvia divinorum* using previously described methodology (Ortega, A.; Blount, J. F.; Manchand, P. S. Salvinorin, *J. Chem. Soc. Perkin Trans.* 1, 1982, 2505-2508; Valdes III, L. J.; Butler, W. M.; Hatfield, G. M.; Paul, A. G.; Koreeda, M. Divinorin A, *J. Org. Chem.* 1984, 49, 4716-4720; and Munro, T. A.; Rizzacasa, M. A., *J. Nat. Prod.* 2003, 66, 703-705). In an attempt to optimize the bioyield of 1, an optimized extraction procedure was identified (FIG. 2). The treatment of 1 using ammonolysis at 0° C. in MeOH resulted in 8a and the C-8 epimer 8b. An alternate method using $Na_2CO_3$ in MeOH afforded a higher yield of 8a and produced significantly less 8b. The acylation of 8a with the appropriate anhydride or acid halide and a catalytic amount of DMAP gave analogues 9-16 in 50-90% yield (FIG. 2). Reacetylation of 8b using acetic anhydride and a catalytic amount of DMAP gave 17, the C-8 epimer of 1.

Figure 3:
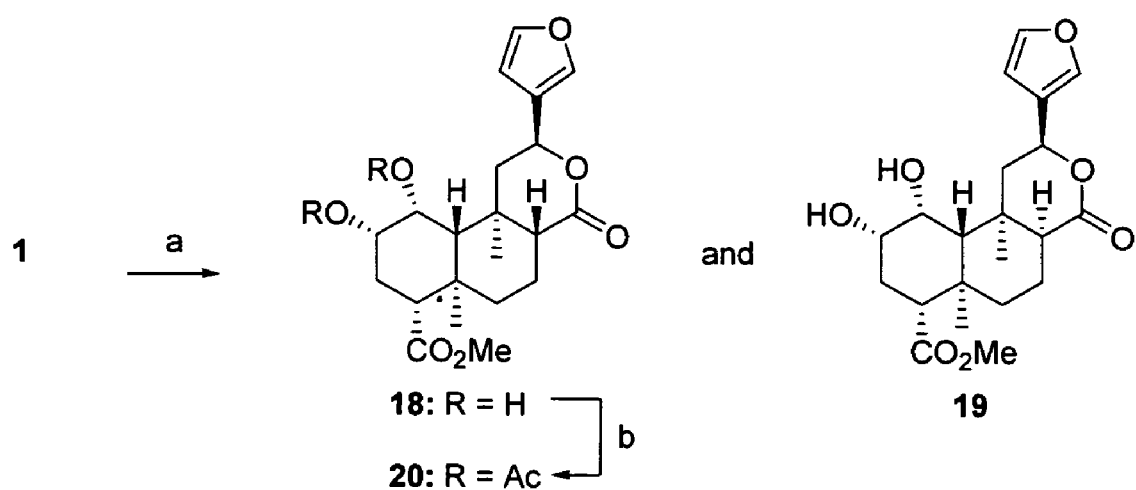
Figure 4:
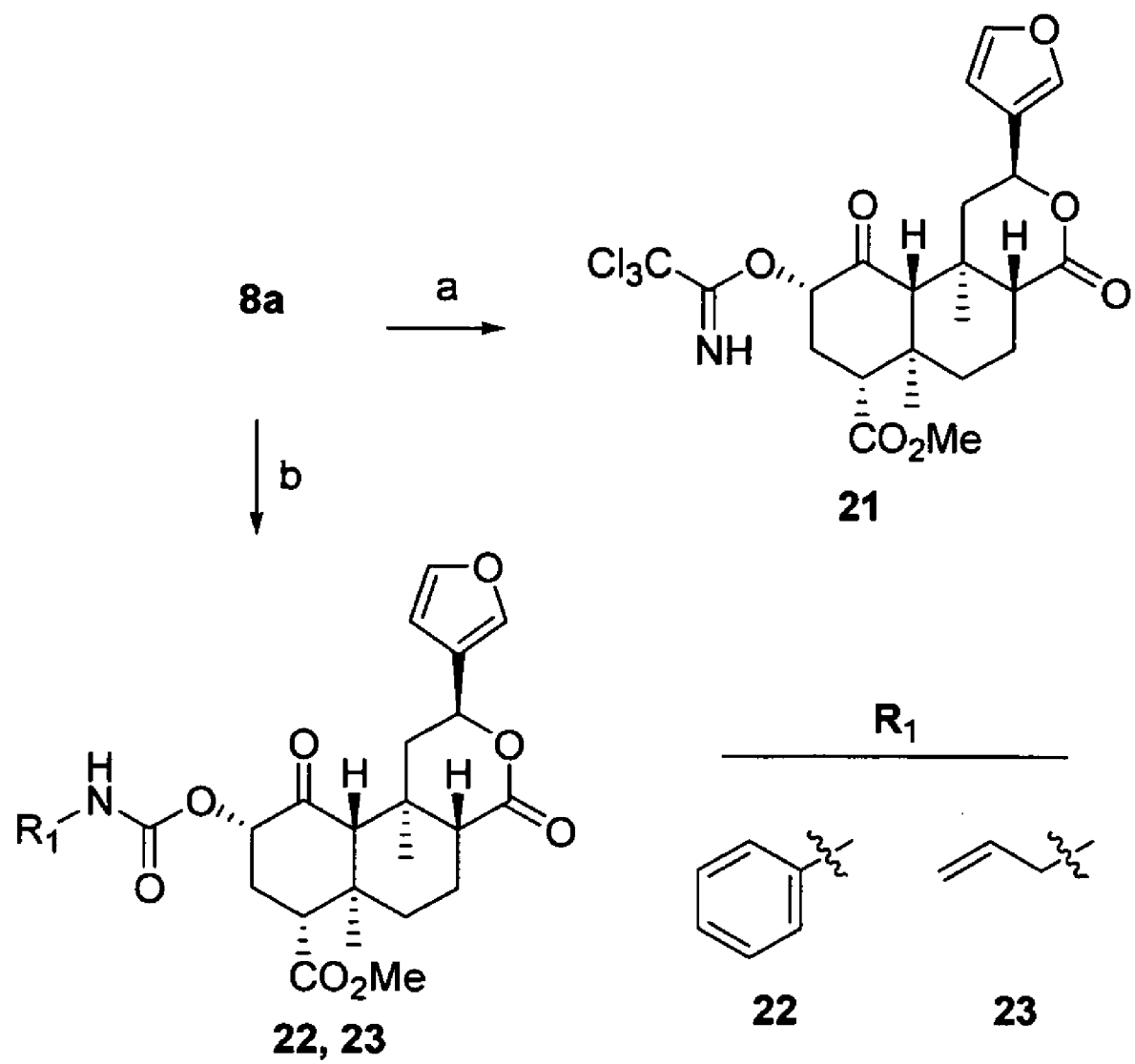

Additional chemistry associated with 1 is described in FIGS. 3 and 4. Reduction of 8a using sodium borohydride in isopropanol at 60° C. gave a mixture of diols 18 and its C-8 epimer 19 (FIG. 3). These compounds were readily separated using column chromatography eluting with a mixture of ethyl acetate/n-hexanes. Treatment of diol 18 with an excess acetic anhydride and a catalytic amount of DMAP in $CH_2Cl_2$ afforded diacetate 20. The reaction of 8a with trichloroacteonitrile and diazobicycloundecene at 0° C. afforded trichloroacetimide 21 in low yield (FIG. 4) (Barton, D. H. R.; Fontana G., *Tetrahedron* 1996, 52, 11163-11176). The reaction of 8a with phenylisocyanate and allyisocyanate in the presence of trimethylsilychloride in $CH_2Cl_2$ gave carbamates 22 and 23 respectively (Villhauer, E. B.; Brinkman, J. A.; Naderi, G. B.; Burkey, B. F.; Dunning, B. E.; Prasad, K.; Mangold, B. L. Russell, M. E.; Hughes, T. E., *J. Med. Chem.* 2003, 46, 26774-2789).

Figure 5:
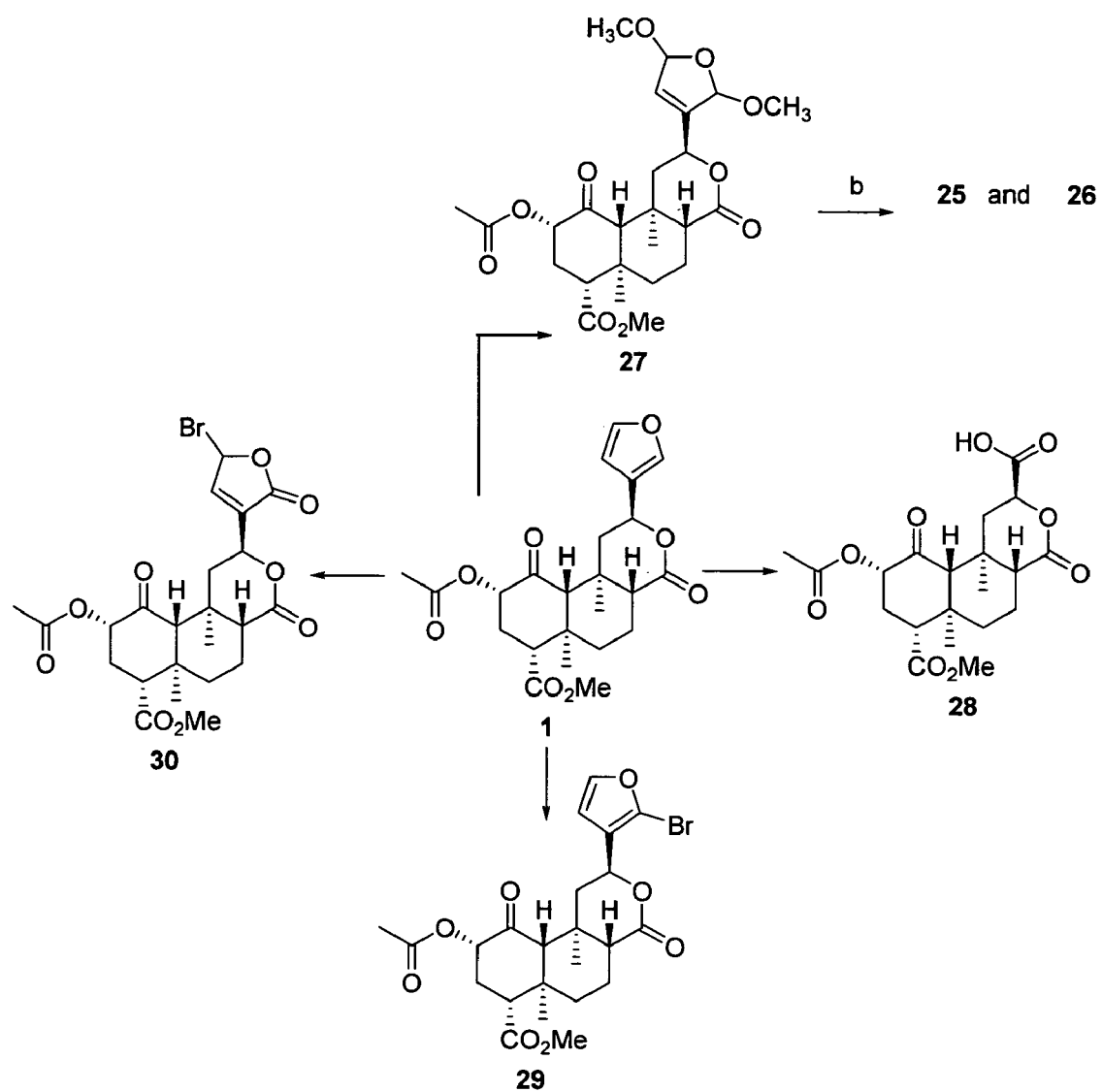

Representative compounds of the invention can also be prepared as illustrated in FIG. 5. The reaction of 1 with bromine in a mixture of $CH_2Cl_2$ and methanol at −30° C. gave 2,5-dimethoxydihydrofuran 27 in 93% yield as a mixture of cis and trans isomers (Fakstorp, J.; et al., *J. Am. Chem. Soc.* 1950, 72, 869-874; Gagnaire, D., Vottero, P. *Bull. Soc. Chim. Fr.* 1963, 2779-2884). The selective oxidation of the cis vs. trans isomers of 27 with $KMnO_4$ in a mixture of THF and $H_2O$ at −10° C. afforded a mixture of salvinicin A (25) and salvinicin B (26) (Honel, M.; Mosher, H. S. *J. Org. Chem.* 1985, 50, 4386-4388). These compounds were readily separated from the unreacted trans isomers of 27 and each other by flash chromatography using a mixture of EtOAc/n-hexanes. Interestingly, 26 was preferentially formed over 25 in an approximately 3:2 ratio, whereas, in the naturally occurring plant, 25 was isolated in higher concentrations than 26 (Harding, W. W. et al., *Org. Lett.* 2005, 7, 3017-3020). The reaction of 1 with $NaIO_4$ and $RuCl_3.3H_2O$ in a mixture of $CCl_4$, acetonitrile, and water afforded acid 28 in 74% yield (Aprile, C., et al., *Tetrahedron* 2003, 59, 2241-2251). This transformation allows for the selective removal of the furan ring. The treatment of 1 with N-bromosuccinimide in acetonitrile at room temperature afforded bromofuran 29 in 38% yield. Longer reaction times led to decomposition of 1. Interestingly, if 1 was reacted with bromine in DMF at 0° C. 29 was not formed.

Rather, dihydrofuran 30 was formed instead. Furthermore, recrystalization of 30 gave a single isomer.

Figure 6:
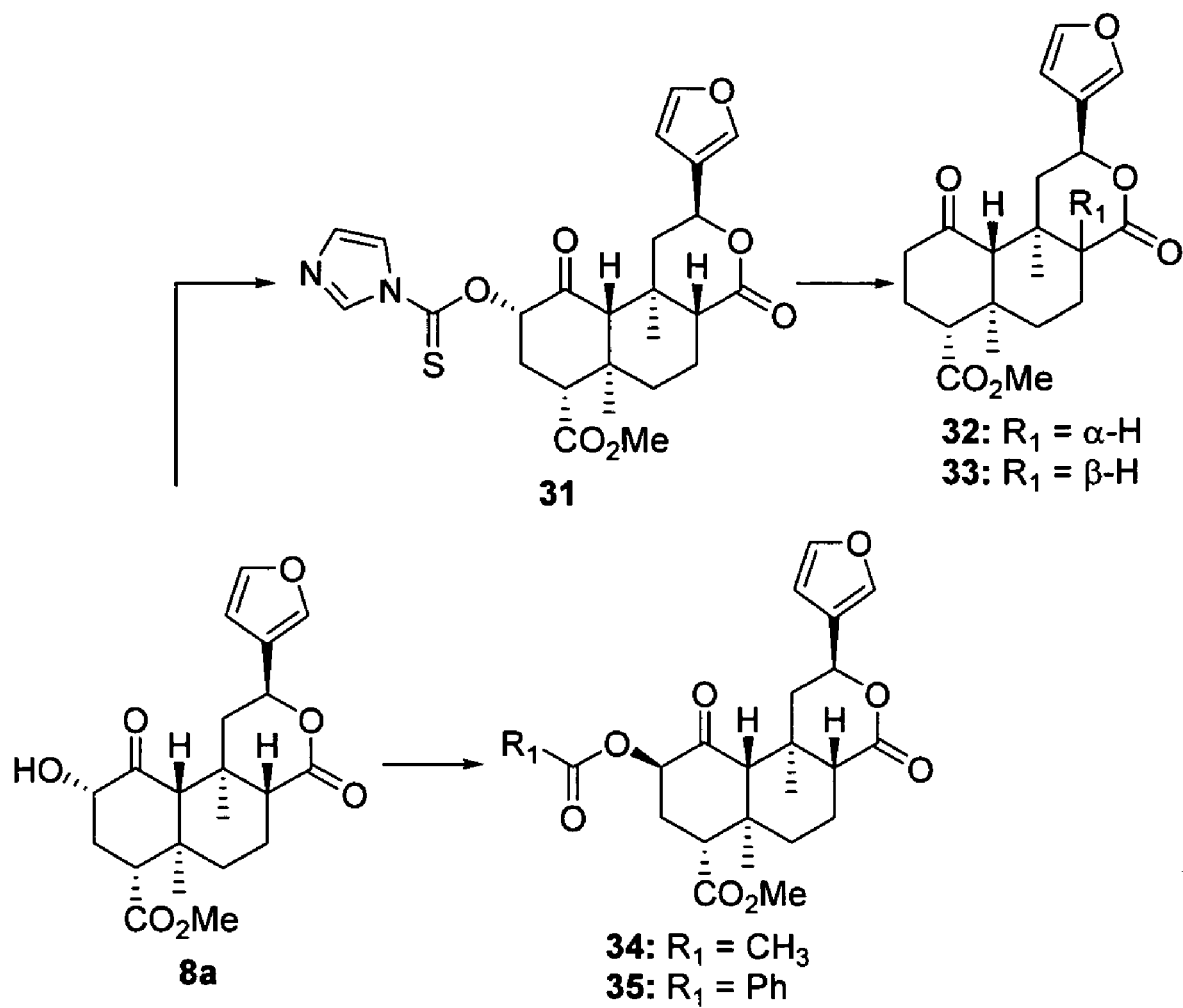

Representative compounds of the invention can also be prepared as illustrated in FIG. 6. The reaction of salvinorin B (8a) with 1,1-thiocarbonyldiimidazole (CDI) and a catalytic amount of DMAP afforded imidazole 31 in 63%. The treatment of imidazole 31 with 2,2'-azobis(2-methylpropionitrile) (AIBN) and tributyltin hydride in toluene afforded an epimeric mixture of 32 and 33 in % yield. The reaction of 8a with acetic acid under modified Mitsunobu conditions (Kiankarimi, M., et al., *Tetrahedron Lett.* 1999, 40, 4497-4500) afforded acetate 34 in 80% yield. Using similar methodology benzoate 35 was also prepared in good yield.

Figure 7:
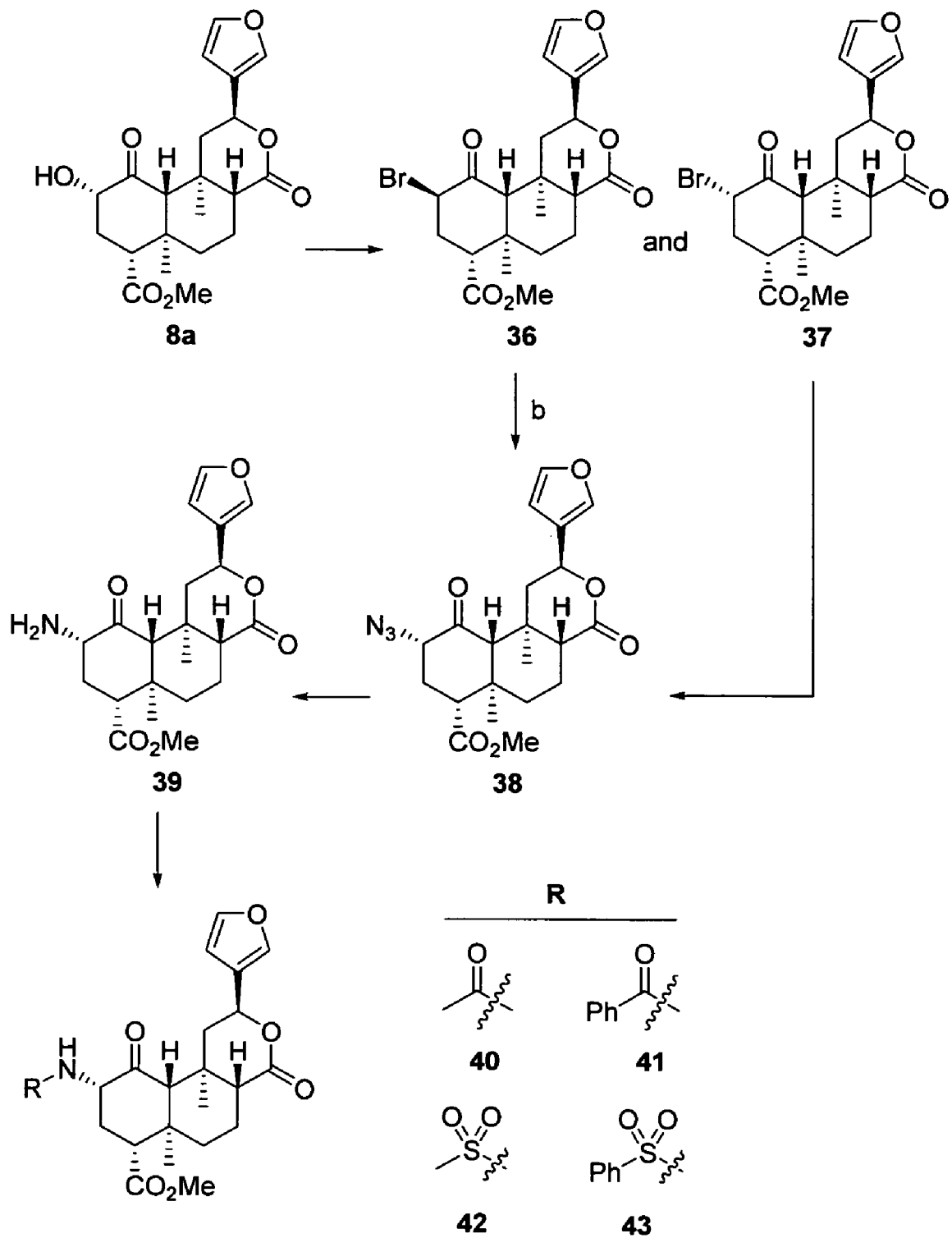
Figure 8:
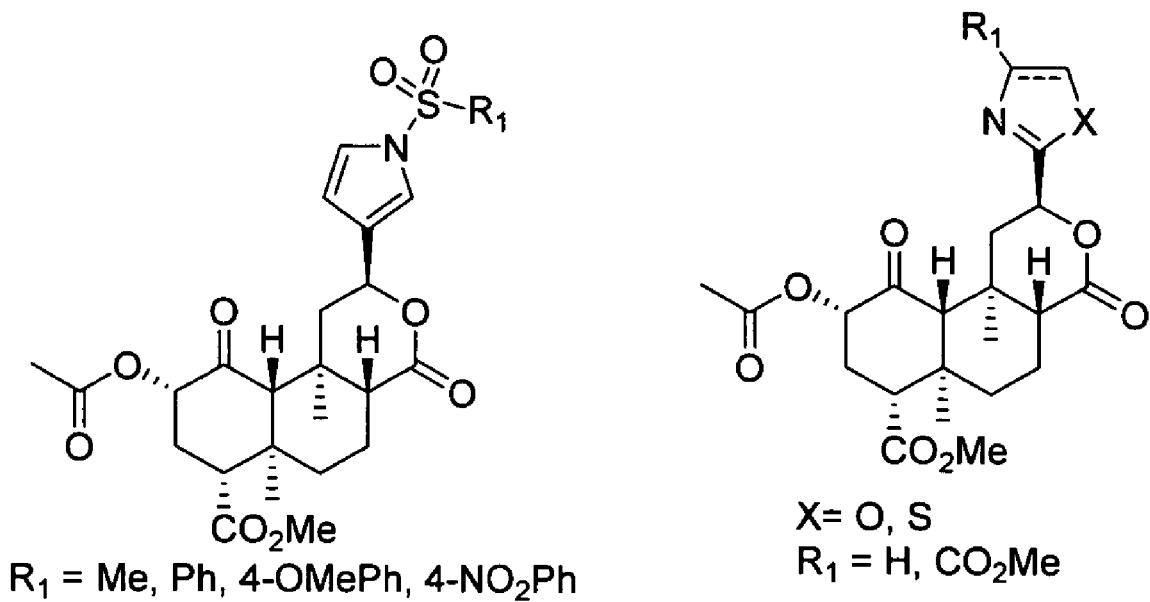
Figure 9:
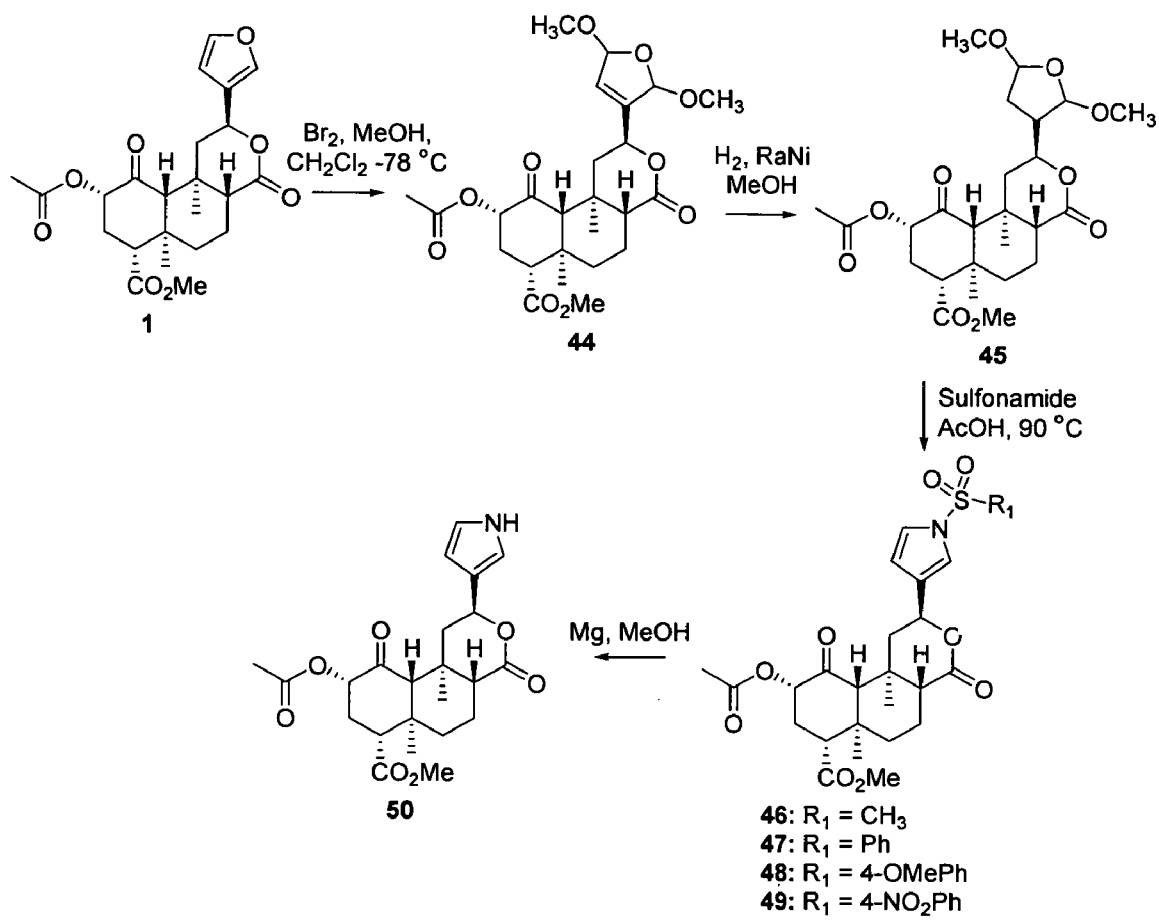
Figure 10:
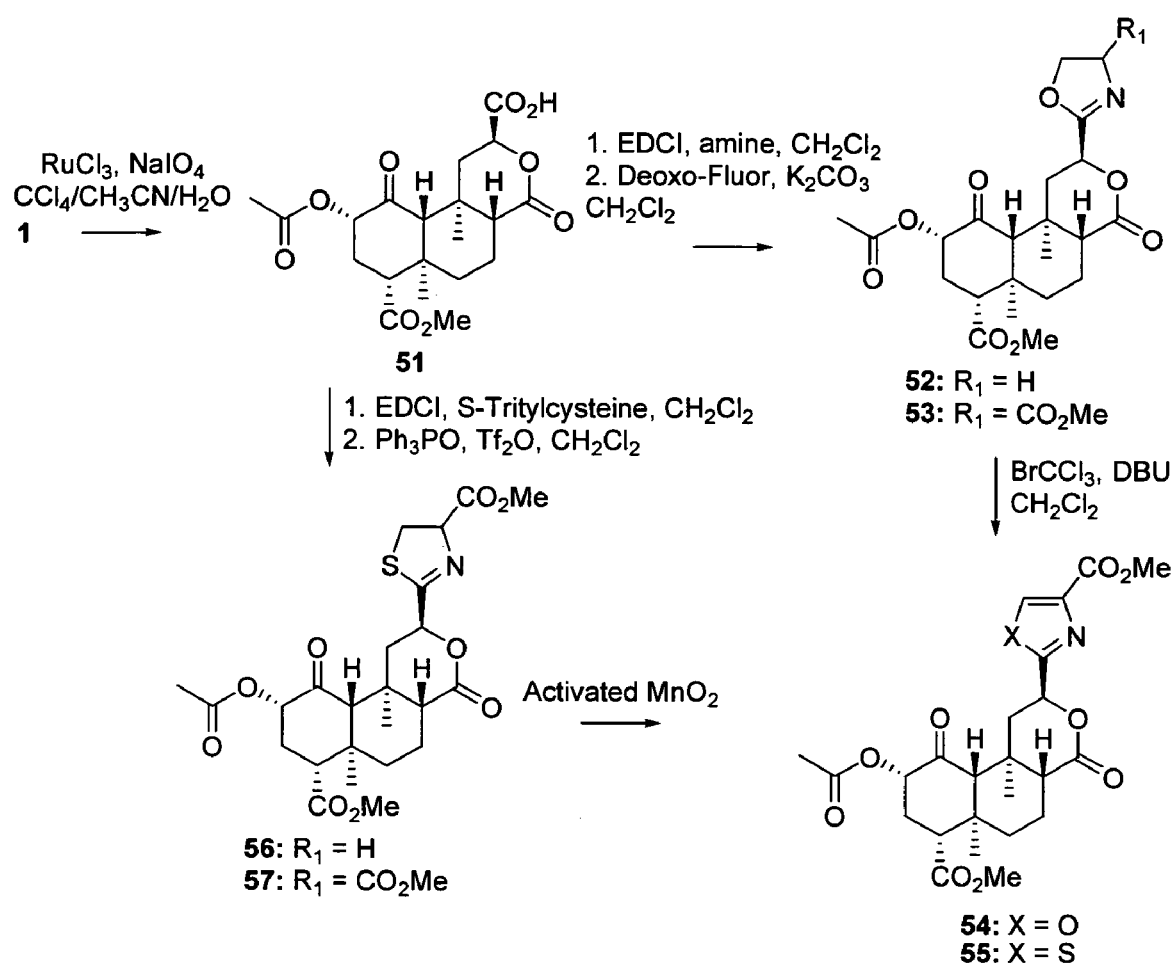
Figure 11:
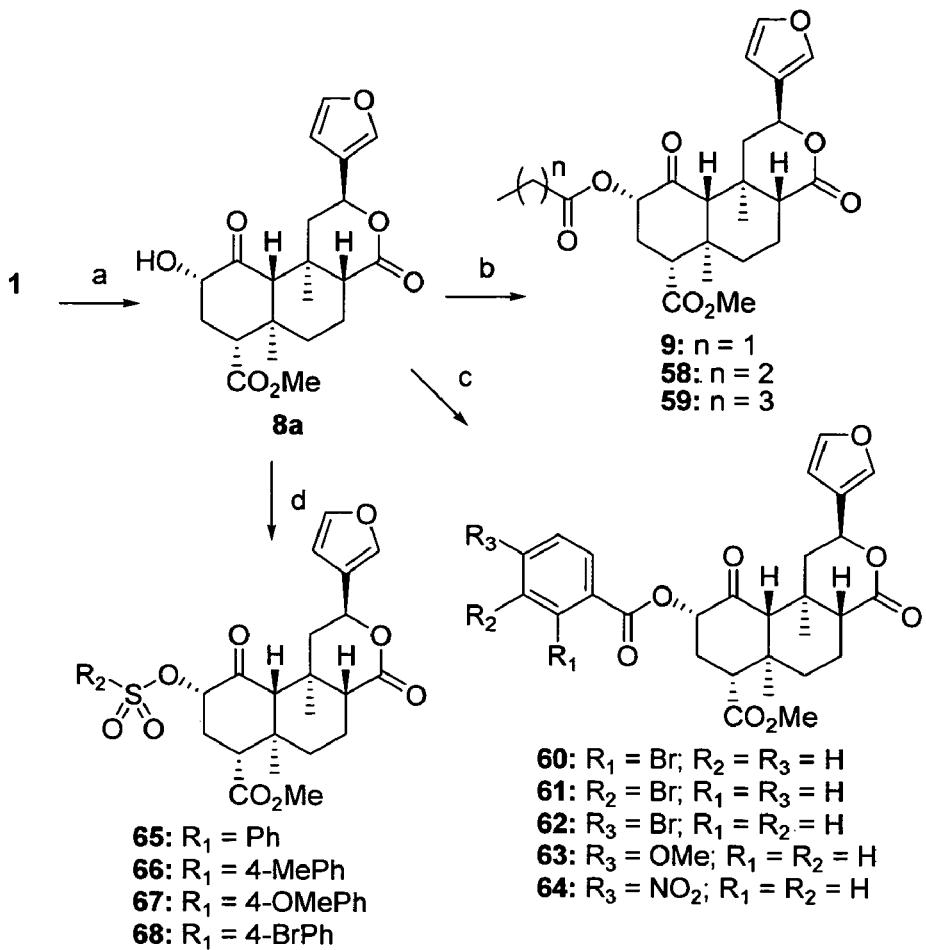

Representative compounds of the invention can also be prepared as illustrated in FIG. 7. The reaction of compound 8a with $CBr_4$ and $PPh_3$ afforded a mixture of the β and α bromides, 36 and 37. However, addition of the $PPh_3$ in two portions afforded exclusively the β isomer. The reaction of 36 in a mixture of acetic acid and DMF, provided the azide 38 in good yield (Aprile, C., et al., *Tetrahedron* 2003, 59, 2241-2251). Reduction of 38 using Zn metal and $NH_4Cl$ afforded amine 39.[25] The treatment of amine 39 with acetic anhydride under basic conditions and in the presence of a catalytic amount of DMAP afforded acetamide 40 (Kiankarimi, M., et al., *Tetrahedron Lett.* 1999, 40, 4497-4500). Using similar conditions and the appropriate anhydride or acid chloride, Compound 39 was also converted to compounds 41, 42, and 43.

The binding affinities of representative compounds of the invention at opioid receptors was determined using [$^{125}$I] IOXY as radioligand (see Ni, Q.; Xu, H.; Partilla, J. S.; de Costa, B. R.; Rice, K. C. et al., *Peptides* 1993, 14, 1279-1293; and de Costa, B. R.; Iadarola, M. J.; Rothman, R. B.; Berman, K. F.; George, C. et al., *J. Med. Chem.* 1992, 35, 2826-2835). As shown previously, 1 was found to have high affinity ($K_i$=1.9 nM) and selectivity for κ receptors (Chavkin, C.; Sud, S.; Jin, W.; Stewart, J.; Zjawiony, J. K. et al., *J. Pharmacol. Exp. Ther.* 2004, 308, 1197-1203). Propionyl derviative 9 was evaluated for affinity at all three opioid receptors to compare with previous data. As expected, 9 had similar affinity compared to 1 at κ receptors ($K_i$=1.8 nM). The addition of a methyl group (10) reduced affinity approximately 10-fold at κ receptors compared to 9 ($K_i$=19 nM vs. $K_i$=1.8 nM). Introduction of an alkene (11) had little effect on κ opioid receptor affinity compared to 10 ($K_i$=42 nM vs. $K_i$=19 nM). However, this modification lead to an approximate 11-fold increase in affinity at κ receptors compared to 10 ($K_i$=260 nM vs. $K_i$=2980 nM). The replacement of the 2-methylacryoyl group with a methyl glyoxyl group (12) resulted in a 10-fold loss of affinity at κ receptors compared to 11 ($K_i$=430 nM vs. $K_i$=42 nM). In addition, this change produced a loss of affinity for μ receptors ($K_i$>10,000 nM).

To further explore the role of size of the 2-position substitutent, benzoate 13 and nicotinate 14 were synthesized (FIG. 2). Introduction of the benzoyl group (13) resulted in a 47-fold loss of affinity at κ receptors compared to 1 ($K_i$=90 nM vs. $K_i$=1.9 nM). Surprisingly, this modification resulted in affinity at 1 receptors ($K_i$=12 nM). This data is believed to represent the first neoclerodane diterpene that binds selectively to the μ opioid receptor. Replacement of benzoyl group with a nicotinoyl group (14) resulted in a 21-fold decrease in affinity at μ receptors compared to 13 ($K_i$=73 nM vs. $K_i$=12 nM) and loss of affinity of κ receptors ($K_i$=1930 nM vs. $K_i$=90 nM).

Replacement of the acetyl group with a mesylate group, i.e. 15, resulted in a compound with similar affinity compared to 1 ($K_i$=2.3 nM vs. $K_i$=1.9 nM). This indicates that there was some degree of tolerability at this particular position. The replacement of the acetyl group with a trimethylsilyl group (16) resulted in an 847-fold loss in affinity at κ receptors compared to 1 (Ki=1610 nM vs. Ki=1.9 nM). Inversion of stereochemistry at the C-8 position (17) resulted in a 75-fold loss in affinity at κ receptors compared to 1 (Ki=300 nM vs. Ki=4 nM). Diol 18 had low affinity at μ and δ receptors whereas, 19 was not found to have significant affinity for any opioid receptors (Ki~10,000 nM) under the conditions tested.

Replacement of the 1-position carbonyl with an α-acetoxy group (20) resulted in a 340-fold decrease in affinity at κ receptors compared to 1 (Ki=650 nM vs. Ki=1.9 nM). Substitution of a trichloroacetimidate (21) resulted in a 34-fold decrease in affinity for κ receptors compared to 1 (Ki=64 nM vs. Ki=1.9 nM). This modification, however, slightly increased affinity for δ receptors (Ki=6470 nM vs. Ki~10,000 nM). The introduction of phenylcarbamoyl group (22) decreased affinity for κ receptors 49-fold compared to 1 (Ki=93 nM vs. Ki=1.9 nM). However, this change resulted in an increase in affinity for μ receptors (Ki=16 nM). It would appear, based on the affinities of 13, 14, and 22 for μ receptors, that the introduction of an aromatic moiety in the 2-position increases μ affinity. Compound 22 had the highest affinity for δ receptors of the series (Ki=230 nM). Finally, the presence of an allylcarbamoyl group 23 resulted in an almost 300-fold decrease in affinity at κ receptors compared to 1 (Ki=120 nM vs. Ki=1.9 nM).

To further explore these developments, 1, 9, 13, and 15 were evaluated for functional activity using a [$^{35}$S]GTPγS assay (Xu, H.; Hashimoto, A.; Rice, K. C.; Jacobson, A. E.; Thomas, J. B. et al., *Synapse* 2001, 39, 64-69). The compounds were found to be agonists.

A recent report has shown that 1 produces a discriminative stimulus effect similar to the high efficacy κ agonist U69,593 in nonhuman primates (Butelman, E. R.; Harrs, T. J.; Kreek, M. J., *Psychopharmacology* 2004, 172, 220-224). In an effort to further understand the in vivo pharmacology of these derivatives, propionate 9 was evaluated for behavioral effects in nonhuman primates in a pilot study. Preliminary results indicate that 9 acts behaviorally as a partial κ agonist. Propionate 9 generalized to U69,593 in only one of two rhesus monkeys tested, up to the highest dose that could be administered (0.1 mg/g, s.c.).

The compounds of the invention can also be administered in combination with other therapeutic agents that are effective to modulate opioid receptor function or to treat a condition such as pain, or alcohol or drug addiction.

The invention will now be illustrated by the following non-limiting Examples.

EXAMPLES

Example 1

Isolation of Salvinorin A (1)

Dried *Salvia divinorum* leaves (1.5 kg), obtained commercially from Ethnogens.com, were ground to a fine powder and percolated with acetone (5×4 L). The acetone extract was concentrated under reduced pressure to afford a crude green gum (93 g), which was subjected to column chromatography on silica gel with elution in n-hexanes containing increasing amounts EtOAc. Fractions eluting in 20% n-hexanes/EtOAc contained salvinorin A (TLC) and other minor diterpenes and some pigmented material. These fractions were pooled and concentrated in vacuo to give a green gum (24 g). A mixture of the crude green gum, acetic anhydride (50 mL, 530 mmol)

and DMAP (0.2 g) in $CH_2Cl_2$ (250 mL) was stirred at RT overnight. The $CH_2Cl_2$ solution was washed sequentially with 1N HCl (2×500 mL), 2N NaOH (100 mL), and $H_2O$ (2×100 mL). The $CH_2Cl_2$ solution was dried ($Na_2SO_4$) and the solvent was removed under reduced pressure to afford a yellow-green gum (23 g). The resulting gum was subjected to column chromatography on silica gel. Elution was performed in 1000 mL aliquots of a mixture of n-hexanes/EtOAc in increments of 10% EtOAc with the final elution in neat EtOAc. Fractions eluting in 30% n-hexanes/EtOAc and subsequent fractions were pooled and the solvent was removed under reduced pressure affording salvinorin A (1 7.5 g, 0.5%) as a green powder, mp 235-238° C. (Lit.[1,2] 240-242° C.).

Example 2

Ammonolysis of Salvinorin A (1)

A mixture of $NH_3$ (6 mL of a 7N solution in MeOH) and 1 (0.4 g, 1.12 mmol) in absolute MeOH (100 mL) was stirred at room temperature overnight. The resulting precipitate was collected by filtration and washed with cold n-hexanes (250 mL) and dried to afford 0.2 g of salvinorin B (8a) as a white solid, mp 211-214° C. (Valdes III, L. J.; Butler, W. M.; Hatfield, G. M.; Paul, A. G.; Koreeda, M. Divinorin A, *J. Org. Chem.* 1984, 49, 4716-4720). The combined filtrate was evaporated to dryness under reduced pressure and the residue was subjected to column chromatography. Eluting in gradient fashion (20% EtOAc/n-hexanes –60% EtOAc/n-hexanes) afforded 8a (0.06 g) and (2S,4aR,6aR,7R,9S,10aS,10bR)-9-(hydroxy)-2-(3-furanyl)dodecahydro-6a,10b-dimethyl-4,10-dioxo-2H-naphtho[2,1-c]pyran-7-carboxylic acid methyl ester (8b, 0.06 g);). $^1$H NMR ($CDCl_3$): δ 1.18 (3H, s, H-19); 1.47 (3H, s, H-20); 1.59-1.66 (3H, m, H-7α,β and H-11β); 1.84 (1H, ddd, J=3.0, 3.0, 9.9 Hz, H-6α); 2.11 (1H, dd, J=2.4, 10.8 Hz, H-8); 2.21 (1H, s, H-10); 2.26 (1H, m, H-6β); 2.47 (2H, m, H-3α,β); 2.55 (1H, dd, J=5.1, 13.5 Hz, H-11α); 2.84 (1H, dd, J=6.9, 9.9 Hz, H-4); 3.63 (1H, d, J=3.3 Hz, OH); 3.75 (3H, S, $CO_2CH_3$); 4.13 (1H, ddd, J=3.2, 7.5, 11.2 Hz, H-2); 5.28 (1H, d, J=10.5 Hz, H-12); 6.39 (1H, dd, J=0.9, 1.8 Hz, H-14); 7.40 (1H, dd, J=1.5, 1.8 Hz, H-15); 7.42 (1H, dd, J=0.9, 1.5 Hz, H-16).

Example 3

(2S,4aS,6aR,7R,9S,10aS,10bR)-9-(hydroxy)-2-(3-furanyl)dodecahydro-6a,10b-dimethyl-4,10-dioxo-2H-naphtho[2,1-c]pyran-7-carboxylic acid methyl ester (8a)

A mixture of 1 (3.5 g, 8.0 mmol) and $Na_2CO_3$ (3.4 g, 32.2 mmol) in absolute MeOH (150 mL) was stirred at room temperature for 4 b. The solvent was removed under reduced pressure and $CH_2Cl_2$ (500 mL) was added to the crude residue. The organic extract was washed successively with 2N HCl (50 mL) and saturated NaCl (50 mL) and dried ($Na_2SO_4$). The solvent was removed under reduced pressure and MeOH (100 mL) was added to the residue. The resulting solid was collected by filtration and dried to afford 2.4 g (77%) of 8a as a white solid, mp 211-214° C. (Lit. 213-216° C.).

Example 4

(2S,4aR,6aR,7R,9S,10aS,10bR)-9-(propionyloxy)-2-(3-furanyl)dodecahydro-6a,10b-dimethyl-4,10-dioxo-2H-naphtho[2,1-c]pyran-7-carboxylic acid methyl ester (9)

A solution of 8a (0.05 g, 0.13 mmol), propionic anhydride (0.09 g, 0.66 mmol) and a catalytic amount of DMAP in $CH_2Cl_2$ (20 mL) was stirred at room temperature overnight. Absolute MeOH (15 mL) was added and the solvent was removed under reduced pressure. $CH_2Cl_2$ (25 mL) was added to the residue and the solution was washed with 10% HCl (3×20 mL) and saturated NaCl (3×20 mL) and dried ($Na_2SO_4$). Removal of the solvent under reduced pressure afforded 9 (0.04 g, 78%) as a white solid, mp 217-221° C.; $^1$H NMR ($CDCl_3$): δ 1.12 (3H, s, H-19); 1.18 (3H, t, J=7.5 Hz, $CH_3CH_2CO_2$); 1.46 (3H, s, H-20); 1.47-1.70 (4H, m, H-6β, H-7α,β, and H-11β); 1.80 (1H, ddd, J=3.0, 3.0, 9.9 Hz, H-6α); 2.07 (1H, dd, J=3.0, 11.1 Hz, H-8); 2.17 (1H, s, H-10); 2.30 (2H, q, J=7.5 Hz, $CH_3CH_2CO_2$); 2.47 (2H, m, H-3α,β); 2.53 (1H, dd, J=5.4, 13.2 Hz, H-11α); 2.76 (1H, dd, J=8.1, 8.7 Hz, H-4); 3.73 (3H, s, $CO_2CH_3$); 5.16 (1H, dd, J=9.9, 10.5 Hz, H-2); 5.53 (1H, dd, J=5.4, 11.7 Hz, H-12); 6.38 (1H, dd, J=0.6, 1.8 Hz, H-14); 7.39 (1H, dd, J=1.5, 1.8 Hz, H-15); 7.41 (1H, dd, J=0.6, 1.5 Hz, H-16).

Example 5

(2S,4aR,6aR,7R,9S,10aS,10bR)-9-(isobutyryloxy)-2-(3-furanyl)-dodecahydro-6a,10b-dimethyl-4,10-dioxo-2H-naphtho[2,1-c]pyran-7-carboxylic acid methyl ester (10)

Using a procedure similar to that described in Example 4 except replacing the propionic anhydride used therein with the requisite anhydride, the title compound 10 (0.04 g, 62%) was prepared as a white solid, mp 209-211° C.; 10 was synthesized as described for 9 from 8a using isobutyryl chloride to afford 0.04 g (62%) of 10 as a white solid, mp 209-211° C.; $^1$H NMR ($CDCl_3$): δ 1.13 (3H, s, H-19); 1.24 (3H, d, J=6.9 Hz, $CH_3CH(CH_3)CO_2$); 1.26 (3H, d, J=6.9 Hz $CH_3CH(CH_3)CO_2$,); 1.46 (3H, s, H-20); 1.52-1.78 (3H, m, H-7α,β and H-11β); 1.80 (1H, ddd, J=3.0, 3.0, 9.9 Hz, H-6α); 2.12 (2H, m, H-3α and H-8); 2.20. (1H, s, H-10); 2.25-2.35 (2H, m, H-3β and H-6β); 2.51 (1H, dd, J=5.1, 13.2 Hz, H-11α); 2.68 (1H, sept, J=6.9 Hz, $CH_3CH(CH_3)CO_2$); 2.77 (1H, dd, J=8.4, 8.4 Hz, H-4); 3.74 (3H, s, $CO_2CH_3$); 5.15 (1H, dd, J=9.9, 10.3 Hz, H-2); 5.52 (1H, dd, J=5.3, 11.9 Hz, H-12); 6.39 (1H, dd, J=0.9, 1.5 Hz, H-14); 7.40 (1H, dd, J=1.5, 1.5 Hz, H-15); 7.42 (1H, dd, J=0.9, 1.5 Hz, H-16).

Example 6

(2S,4aR,6aR,7R,9S,10aS,10bR)-9-(2-methylacryloyloxy)-2-(3-furanyl)-dodecahydro-6a,10b-dimethyl-4,10-dioxo-2H-naphtho[2,1-c]pyran-7-carboxylic acid methyl ester (11)

Using a procedure similar to that described in Example 4 except replacing the propionic anhydride used therein with the requisite anhydride, the title compound (0.03 g, 56%) was prepared as a white solid, mp 196-199° C.; $^1$H NMR ($CDCl_3$): δ 1.15 (3H, s, H-19); 1.47 (3H, s, H-20); 1.50-1.75 (4H, m, H-6β, H-7α,β and H-11β); 1.82 (1H, ddd, J=3.0, 3.0, 10.2 Hz, H-6α); 1.99 (3H, s, $CH_2$=C($CH_3$)$CO_2$); 2.04-2.21 (2H, m, H-3α and H-8); 2.23 (1H, s, H-10); 2.40 (1H, m, H-3β); 2.53

(1H, dd, J=5.1, 13.5 Hz, H-11α); 2.80 (1H, dd, J=8.4, 8.4 Hz, H-4); 3.75 (3H, s, CO$_2$CH$_3$); 5.22 (1H, dd, J=9.9, 9.9 Hz, H-2), 5.53 (1H, dd, J=5.1, 11.7 Hz, H-12), 5.69 (1H, d, J=1.5 Hz, H—CH═C(CH$_3$)CO$_2$), 6.24 (1H, d, J=1.5 Hz, H—CH═C(CH$_3$)CO$_2$), 6.39 (1H, dd, J=0.9, 1.5 Hz, H-14), 7.41 (1H, dd, J=1.5, 1.5 Hz, H-15), 7.42 (1H, dd, J=0.9, 1.5 Hz, H-16).

Example 7

Oxalic acid methyl ester (2S,4aR,6aR,7R,9S,10aS,10bR)-7-carbomethoxy-2-(3-furanyl)dodecahydro-6a,10b-dimethyl-4,10-dioxo-2H-naphtho[2,1-c]pyran-9-yl ester (12)

Using a procedure similar to that described in Example 4 except replacing the propionic anhydride used therein with methyl chlorooxoacetate, the title compound (26%) was prepared as a white solid, mp 241-244° C.; $^1$H NMR (CDCl$_3$): δ 1.16 (3H, s, H-19); 1.47 (3H, s, H-20); 1.56-1.81 (4H, m, H-3α, H-6β, H-7β and H-11β); 1.84 (1H, ddd, J=3.0, 3.0, 10.1 Hz, H-6α); 2.11 (1H, dd, J=3.0, 11.3 Hz, H-8); 2.19 (1H, m, H-7α); 2.22 (1H, s, H-10); 2.46 (1H, dd, J=4.5, 8.1 Hz, H-3β); 2.52 (1H, dd, J=5.6, 12.8 Hz, H-11α); 2.79 (1H, dd, J=5.1, 12.0 Hz, H-4); 3.76 (3H, s, CO$_2$CH$_3$); 3.96 (3H, s, COCO$_2$CH$_3$); 5.26 (1H, dd, J=8.5, 11.9 Hz, H-2); 5.54 (1H, dd, J=5.1, 11.7 Hz, H-12); 6.39 (1H, dd, J=0.9, 1.5 Hz, H-14); 7.42 (2H, m, H-15 and H-16).

Example 8

(2S,4aR,6aR,7R,9S,10aS,10bR)-9-(benzoyloxy)-2-(3-furanyl)-dodecahydro-6a,10b-dimethyl-4,10-dioxo-2H-naphtho[2,1-c]pyran-7-carboxylic acid methyl ester (13)

A solution of 8a (0.05 g, 0.13 mmol), benzoyl chloride (0.09 g, 0.92 mmol) and a catalytic amount of DMAP in CH$_2$Cl$_2$ (20 mL) was stirred at room temperature for 2 h. Absolute MeOH (15 mL) was added and the solvent was removed under reduced pressure. CH$_2$Cl$_2$ (25 mL) was added to the residue and the solution was washed with 10% HCl (3×20 mL) and saturated NaCl (3×20 mL) and dried (Na$_2$SO$_4$). Removal of the solvent under reduced pressure afforded 13 (0.06 g, 98%) as a white solid, mp 165-170° C.; $^1$H NMR (CDCl$_3$): δ 1.18 (3H, s, H-19); 1.47 (3H, s, H-20); 1.50-1.75 (4H, m, H-6β, H-7α,β and H-11β); 1.84 (1H, ddd, J=3.0, 3.0, 9.9 Hz, H-6α); 2.11 (1H, dd, J=2.4, 10.8 Hz, H-8); 2.26 (1H, s, H-10); 2.47 (2H, m, H-3α,β); 2.55 (1H, dd, J=5.1, 13.5 Hz, H-11α); 2.84 (1H, dd, J=6.9, 9.9 Hz, H-4); 3.75 (3H, s, CO$_2$CH$_3$); 5.40 (1H, dd, J=9.6, 10.5 Hz, H-2); 5.52 (1H, dd, J=2.1, 11.7 Hz, H-12); 6.39 (1H, dd, J=0.9, 1.8 Hz, H-14); 7.40 (1H, dd, J=1.5, 1.8 Hz, H-15); 7.42 (1H, dd, J=0.9, 1.5 Hz, H-16); 7.48 (2H, dt, J=7.2, 7.5 Hz, Ar-meta-H); 7.60 (1H, tt, J=1.2, 7.5 Hz, Ar-para-H); 8.09 (2H, dt, J=1.2, 7.2 Hz, Ar-ortho-H).

Example 9

Nicotinic acid (2S,4aR,6aR,7R,9S,10aS,10bR)-7-carbomethoxy-2-(3-furanyl)dodecahydro-6a,10b-dimethyl-4,10-dioxo-2H-naphtho[2,1-c]pyran-9-yl ester (14)

Using a procedure similar to that described in Example 8, except replacing the benzoyl chloride used therein with nicotinoyl chloride hydrochloride the title compound 14 (0.03 g, 56%) was prepared as a white solid, mp 200-204° C.; $^1$H NMR (CDCl$_3$): δ 1.18 (3H, s, H-19); 1.47 (3H, s, H-20); 1.50-1.72 (4H, m, H-6β, H-7α,β and H-11β); 1.84 (1H, ddd, J=3.0, 3.0, 9.9 Hz, H-6α); 2.11 (1H, dd, J=2.4, 10.5 Hz, H-8); 2.27 (1H, s, H-10); 2.49 (2H, m, H-3α,β); 2.54 (1H, dd, J=5.1, 13.2 Hz, H-11α); 2.85 (1H, dd, J=6.2, 10.7 Hz, H-4); 3.76 (3H, s, CO$_2$CH$_3$); 5.41 (1H, dd, J=10.1, 10.1 Hz, H-2); 5.53 (1H, dd, J=5.1, 11.7 Hz, H-12); 6.39 (1H, d, J=0.9 Hz, H-14); 7.42 (3H, m, H-15, H-16 and Ar—H); 8.34 (1H, ddd, J=1.5, 3.9, 7.8 Hz, Ar—H); 8.82 (1H, ddd, J=1.8, 3.9 Hz, Ar—H); 9.27 (1H, d, J=1.5 Hz, Ar—H).

Example 10

(2S,4aR,6aR,7R,9S,10aS,10bR)-9-(methanesulfonyloxy)-2-(3-furanyl)-dodecahydro-6a,10b-dimethyl-4,10-dioxo-2H-naphtho[2,1-c]pyran-7-carboxylic acid methyl ester (15)

A solution of 8a (0.05 g, 0.13 mmol), methanesulfonyl chloride (1 mL) and NEt$_3$ (2 mL) in CH$_2$Cl$_2$ (30 mL) was stirred at room temperature overnight and then the mixture was washed with saturated NaHCO$_3$ (20 mL) and saturated NaCl (2×15 mL) and dried (Na$_2$SO$_4$). The solvent was removed under reduced pressure. The resulting crude solid was purified by column chromatography (eluent: ethyl acetate/n-hexanes) to afford 0.02 g (32%) of a white solid, mp 147-150° C.; $^1$H NMR (CDCl$_3$): δ 1.14 (3H, s, H-19); 1.47 (3H, s, H-20); 1.50-1.70 (3H, m, H-7α,β and H-11β); 1.81 (1H, m, H-6α); 2.11 (1H, dd, J=2.9, 11.3 Hz, H-8); 2.16 (1H, s, H-10); 2.19 (1H, m, H-6β); 2.42 (1H, dd, J=13.2, 13.2 Hz, H-3α); 2.50 (1H, m, H-3β); 2.52 (1H, dd, J=4.8, 13.2 Hz, H-11α); 2.75 (1H, dd, J=3.6, 13.2 Hz, H-4); 3.25 (3H, s, CH$_3$SO$_2$); 3.74 (3H, s, CO$_2$CH$_3$); 5.07 (1H, dd, J=8.0, 12.2 Hz, H-2); 5.55 (1H, dd, J=5.1, 11.7 Hz, H-12); 6.41 (1H, dd, J=0.9, 1.8 Hz, H-14); 7.42 (1H, dd, J=1.8, 1.8 Hz, H-15); 7.45 (1H, br d).

Example 11

(2S,4aR,6aR,7R,9S,10aS,10bR)-9-(trimethylsilanyloxy)-2-(3-furanyl)-dodecahydro-6a,10b-dimethyl-4,10-dioxo-2H-naphtho[2,1-c]pyran-7-carboxylic acid methyl ester (16)

A solution of 8a (0.08 g, 0.20 mmol), NEt$_3$ (0.1 mL, 0.72 mmol) and chlorotrimethylsilane (0.1 mL, 0.79 mmol) in CH$_2$Cl$_2$ (30 mL) was stirred at room temperature overnight. The mixture was washed with saturated NaHCO$_3$ (2×10 mL) and H$_2$O (50 mL), dried (Na$_2$SO$_4$), and the solvent was removed under reduced pressure. The resulting crude solid was purified by column chromatography (eluent: ethyl acetate/nhexanes) to afford 16 (0.06 g, 68%) as a white solid, mp 197-200° C.; $^1$H NMR (CDCl$_3$): δ 0.14 (9H, s, (CH$_3$)$_3$SiO; 1.11 (3H, s, H-19); 1.48 (3H, s, H-29); 1.50-1.73 (3H, m, H-7α,β and H-11β); 1.79 (1H, ddd, J=3.0, 3.0, 10.5 Hz, H-6α); 2.03 (1H, dd, obscured, H-8); 2.06 (1H, s, H-10); 2.10-2.38 (3H, m, H-3α,β and H-6β); 2.57 (1H, dd, J=5.1, 10.5 Hz, H-11α); 2.69 (1H, dd, J=3.9, 12.9 Hz, H-4); 3.72 (3H, s, CO$_2$CH$_3$); 4.12 (1H, dd, J=7.5, 11.7 Hz, H-2); 5.56 (1H, dd, J=5.1, 11.4 Hz, H-12); 6.38 (1H, dd, J=0.8, 1.7 Hz, H-14); 7.40 (1H, m, H-15); 7.42 (1H, m, H-16).

Example 12

(2S,4aR,6aR,7R,9S,10aS,10bR)-9-(Acetyloxy)-2-(3-furanyl)dodecahydro-6a,10b-dimethyl-4,10-dioxo-2H-naphtho[2,1-c]pyran-7-carboxylic acid methyl ester (17)

Using a procedure similar to that described in Example 4 except replacing the propionic anhydride used therein with acetic anhydride, the title compound 17 (0.04 g, 61%) was prepared as a clear oil: $^1$H NMR (CDCh): δ1.06 (s, 3H); 1.54 (m, 2H); 1.63 (s, 3H); 1.84 (ddt, Ja=3.9, Jb=14.1, Jc=14.1, 1H), 1.99 (dd, Ja=3.4, Jc=13.4, 1H), 2.09 (s, 1H); 2.16 (s, 3H); 2.20-2.32 (m, 3H); 2.37 (dd, Ja=2.3, Jb=14.9, 1H); 2.46 (d, J=2.7, 1H); 2.77 (dd, Ja=8.4, Jb=8.4, 1H); 3.70 (s, 3H); 5.12 (dd, Ja=9.9, Jb=9.9, 1H); 5.27 (br d, 1H); 6.38 (m, 1H); 7.39 (m, 1H); 7.44 (m, 1H).

Example 13

Sodium Borohydride Reduction of Savinorin A (1)

NaBH$_4$ (0.16 g, 0.16 mmol) was added to a stirred solution of Savinorin A (1) (0.16 g, 0.37 mmol) in 2-propanol (50 mL) and the resulting mixture was heated at 60° C. for 6 h. The solvent was removed under reduced pressure and CHCl$_3$ (100 mL) was added to the residue. The CHCl$_3$ solution was washed successively with 2N HCl (2×30 mL), saturated NaHCO$_3$ (2×30 mL), and H$_2$0 (50 mL) and dried (Na$_2$SO$_4$) Removal of the solvent under reduced pressure afforded a crude solid. The crude solid was purified using column chromatography eluting in gradient fashion (30% EtOAc/nhexanes –60% EtOAc/n-hexanes) to afford a mixture of 18 (0.08 g) and 19 (0.04 g). (2S,4aR,6aR,7R,9S,10R,10aS,10bR)-9,10-(dihydroxy)-2-(3-furanyl)dodecahydro-6a,10b-dimethyl-4-oxo-2H-naphtho[2,1-c]pyran-7-carboxylic acid methyl ester (18). White solid, mp 105-108° C.; $^1$H NMR (CDCl$_3$): δ 0.92 (d, J=1.8, 1H); 1.38 (s, 3H); 1.47 (s, 3H); 1.53-1.82 (m, 6H); 1.92 (m, 1H); 2.01-2.23 (m, 3H); 2.06 (s, 1H); 2.35-2.55 (dd, J$_a$=5.1, J$_b$=12.9, 1H); 3.40-3.61 (m, IH); 3.68 (s, 3H); 4.20 (br s, 1H); 5.57 (dd, J$_a$=5.4, J$_b$=11.4, IH); 6.42 (m, 1H); 7.40 (m, 1H); 7.47 (m, 1H). (2S,4aS,6aR,7R,9S,10R,10aS,10bR)-9,10-(dihydroxy)-2-(3-furanyl)dodecahydro-6a,10b-dimethyl-4-oxo-2H-naphtho[2,1-c]pyran-7-carboxylic acid methyl ester (19). White solid, mp 199-201° C.; $^1$H NMR (CDCl$_3$): δ 0.92 (br s, 1H); 1.33 (s, 3H); 1.54 (dt, J$_a$=3.4, J$_b$=13.5, 1H); 1.67 (s, 3H); 1.69-1.78 (m, 2H); 1.84-1.94 (m, 2H); 2.12-2.26 (m, 4H); 2.29 (s, 1H); 2.47 (d, J=3.9, 1H); 3.52-3.58 (m, 1H); 3.67 (m, 3H); 4.08 (br s, 1H); 5.30 (d, J=11.4, 1H); 6.43 (m, 1H); 7.44 (m, 1H); 7.50 (m, 1H).

Example 14

(2S,4aR,6aR,7R,9S,10R,10aS,10bR)-9,10-(diacetoxy)-2-(3-furanyl)dodecahydro-6a,10b-dimethyl-4-oxo-2H-naphtho[2,1-c]pyran-7-carboxylic acid methyl ester (20)

A solution of 18 (0.02 g, 0.05 mmol), acetic anhydride (2 mL, 21.2 mmol), NEt$_3$ (4 mL, 28.7 mmol) and a catalytic amount of DMAP was stirred at room temperature for 3 hours. The solution was then poured into 2N NaOH (20 mL) and the resulting mixture was extracted with CH$_2$Cl$_2$ (30 mL). The CH$_2$Cl$_2$ portion was washed with 2N HCl (10 mL) and H$_2$O (2×20 mL) and dried (Na$_2$SO$_4$). Removal of the solvent under reduced pressure afforded a brown oil that was purified by column chromatography (eluent: ethyl acetate/n-hexanes) to afford 20 (0.01 g, 60%) as a colorless oil; $^1$H NMR (CDCl$_3$): δ 1.19 (s, 3H); 1.39 (s, 3H); 1.58-1.90 (m, 5H); 1.99 (s, 3H); 2.01-2.13 (m, 2H); 2.15 (s, 3H); 2.20-2.38 (m, 3H); 2.44 (dd, J$_a$=5.4, J$_b$=13.2, 1H); 3.71 (s, 3H); 4.77 (m, 1H); 5.47 (dd, J$_a$=5.6, J$_b$=11.6, 1H); 5.68 (br s, 1H); 6.43 (dd, J$_a$=0.8, J$_b$=1.7, 1H); 7.42 (m, 1H); 7.46 (m, 1H).

Example 15

(2S,4aR,6aR,7R,9S,10aS,10bR)-9-(2,2,2-trichloroacetimidoyloxy)-2-(3-furanyl)-dodecahydro-6a,10b-dimethyl-4,10-dioxo-2H-naphtho[2,1-c]pyran-7-carboxylic acid methyl ester (21)

A solution of 8a (0.05 g, 0.13 mmol), trichloroacetonitrile (0.1 mL, 1.0 mmol), 1,8-Diazobicylo[5.4.0]undec-7-ene (0.05 mL, 0.3 mmol) in dichloroethane (20 mL) was stirred at 0° C. for 24 h. The reaction mixture was then washed with saturated NaHCO$_3$ (10 mL) and H$_2$O (10 mL) and dried (Na$_2$SO$_4$). The solvent was removed under reduced pressure to give a crude oil. The oil was purified by column chromatography (eluent: ethyl acetate/n-hexanes) to afford 21 (0.02 g, 37%) as a white solid, mp 120-123° C.; $^1$H NMR (CDCl$_3$): δ 1.18 (s, 3H); 1.50 (s, 3H); 1.52-1.76 (m, 4H); 1.85 (dd, J$_a$=2.6, J$_b$=10.1, 1H); 2.10 (dd, J$_a$=2.9, J$_b$=11.6, 1H); 2.20 (m, 1H); 2.24 (s, 1H); 2.35-2.58 (m, 3H); 2.80 (dd, J$_a$=4.1, J$_b$=12.5, 1H); 3.75 (s, 3H); 5.34 (dd, J$_a$=7.7, J$_b$=12.2, 1H); 6.40 (dd, J$_a$=0.9, J$_b$=1.5, 1H); 7.41 (dd, 1H, 1.5, 1.5, 1H); 7.43 (dd, J$_a$=0.9, J$_b$=1.5, 1H); 8.38 (s, 1H).

Example 16

(2S,4aR,6aR,7R,9S,10aS,10bR)-9-(phenylcarbamoyloxy)-2-(3-furanyl)-dodecahydro-6a,10b-dimethyl-4,10-dioxo-2H-naphtho[2,1-c]pyran-7-carboxylic acid methyl ester (22)

A solution of 8a (0.06 g, 0.14 mmol), trimethylsilyl chloride (0.01 mL, 0.08 mmol) and phenylisocyanate (0.1 mL, 0.92 mmol) in CH$_2$Cl$_2$ was stirred at room temperature for 5 days. The reaction mixture was then washed with saturated NaHCO$_3$ (10 mL) and H$_2$O (10 mL) and dried (Na$_2$SO$_4$). The solvent was removed under reduced pressure to give a crude oil. The oil was purified by column chromatography (eluent: ethyl acetate/n-hexanes) to afford 22 (0.01 g, 14%) as a clear oil: $^1$H NMR (CDCl$_3$): δ 1.15 (s, 3H); 1.48 (s, 3H); 1.52-1.72 (m, 3H); 1.82 (dd, 1H, 2.7, 10.2 1H); 2.03-2.20 (m, 1H); 2.22 (s, 1H); 2.24-2.48 (m, 2H); 2.54 (dd, J$_a$=5.1, J$_b$=13.5, 1H); 2.80 (dd, J$_a$=3.6, J$_b$=13.2, 1H); 3.75 (s, 3H); 5.21 (dd, J$_a$=7.8, J$_b$=12.3, 1H); 5.54 (dd, J=11.7, 1H); 6.40 (m, 1H), 6.69 (br s, 1H); 6.87 (br s, 1H); 7.12 (m, 2H); 7.28-7.45 (m, 5H).

Example 17

(2S,4aR,6aR,7R,9S,10aS,10bR)-9-(allylcarbamoyloxy)-2-(3-furanyl)-dodecahydro-6a,10b-dimethyl-4,10-dioxo-2H-naphtho[2,1-c]pyran-7-carboxylic acid methyl ester (23)

Using a procedure similar to that described in Example 16, except replacing the phenylisocyanate with allylisocyanate, the title compound 23 was prepared as a white solid (0.01 g, 17%), mp 196-199° C.; $^1$H NMR (CDCl$_3$): δ 1.13 (s, 3H); 1.48 (s, 3H); 1.50-1.76 (m, 3H); 1.80 (dd, J$_a$=2.7, J$_b$=9.9, 1H); 2.10 (dd, J$_a$=3.1, J$_b$=11.1, 1 Hz); 2.19 (s, 1H); 2.20-2.40 (m, 1H); 2.55 (dd, J$_a$=5.4, J$_b$=13.5, 1H); 2.76 (dd, J$_a$=3.9, $J_b$=13.2, 1H); 3.74 (s, 3H); 3.84 (dd, $J_a$=5.4, $J_b$=5.4, 2H); 4.98 (t, J=5.4, 1H); 5.12 (dd, $J_a$=7.8, $J_b$=12.3, 1H); 5.18 (dd, $J_a$=1.2, $J_b$=10.2, 1H); 5.25 (dd, $J_a$=1.2, $J_b$=17.1, 1H); 5.54 (dd, $J_a$=5.4, $J_b$=11.4, 1H); 5.86 (ddt, $J_a$=5.4, $J_b$=10.2, $J_c$=11.4, 1H); 6.40 (dd, $J_a$=1.5, $J_b$=1.8, 1H); 7.41 (dd, $J_a$=0.9, $J_b$=1.5 1H); 7.43 (dd, $J_a$=0.9, $J_b$=1.5, 1H).

Example 18

Synthesis of [2,2,2-$^2$H$_3$]salvinorin A (24)

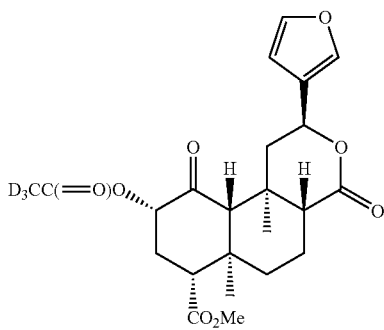

A solution of 8a (0.1 g, 0.3 mmol), d$_6$-acetic anhydride (0.1 g, 1.3 mmol) and a catalytic amount of DMAP in CH$_2$Cl$_2$ (20 mL) was stirred at room temperature for 2 hours. Absolute MeOH (15 mL) was added and the solvent was removed under reduced pressure. CH$_2$Cl$_2$ (25 mL) was added to the residue and the solution was washed with 10% HCl (3×20 mL) and saturated NaCl (3×20 mL) and dried (Na$_2$SO$_4$). Removal of the solvent under reduced pressure afforded 24 (0.09 g, 80%) as a white solid, mp 237-240° C.: $^1$H NMR (300 MHz, CDCl$_3$) δ 1.12 (s, 3H), 1.46 (s, 3H), 1.80 (m, 1H), 2.07 (dd, J=3.0, 11.6 Hz, 1H), 2.31 (m, 2H), 2.51 (dd, J=5.4, 13.2 Hz, 1H), 2.75 (dd, J=6.3, 10.2 Hz, 1H), 3.73 (s, 3H), 5.15 (dd, J=9.9, 9.9 Hz, 1H), 5.53 (dd, J=4.8, 12.0 Hz, 1H), 6.37 (dd, J=0.9, 1.5 Hz, 1H), 7.39 (dd, J=1.5, 1.8 Hz, 1H), 7.41 (dd, J=0.9, 1.5 Hz, 1H).

Example 19

Isolation of Salvinicin A (25)

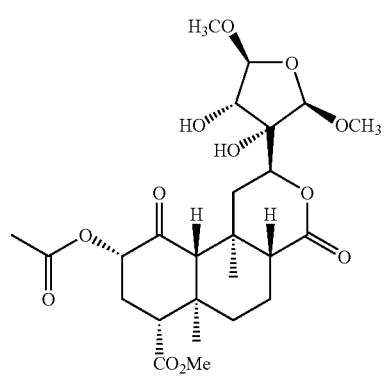

S. divinorum leaves were percolated with acetone and the acetone was removed in vacuo to afford a crude green gum (92.0 g). The crude acetone extract was subjected to flash column chromatography on silica gel with elution in n-hexanes containing increasing amounts EtOAc with initial elution in 10% EtOAc/n-hexanes and final elution in neat EtOAc. Fractions eluted in 80% EtOAc/n-hexane and subsequent fractions were pooled, the solvent removed in vacuo and the crude plant material (28.0 g) rechromatographed. Elution was performed in 1000 mL aliquots of a mixture of n-hexanes in EtOAc with increments of 10% EtOAc with the initial elution in 30% EtOAc/n-hexanes and final elution in neat EtOAc. Fractions eluted in 70% EtOAc/n-hexanes and subsequent fractions were combined, the solvent removed in vacuo and the crude material (12.1 g) re-subjected to flash column chromatography. Elution was performed in 2% MeOH/CH$_2$Cl$_2$ (250 mL aliquots; fractions 1-22) and finally with MeOH. The MeOH fraction was concentrated in vacuo and subjected to repeated flash column chromatography performed in 2% MeOH/CH$_2$Cl$_2$ to yield compounds 25 (65 mg) and 26 (14 mg) respectively; Salvinicin A (25) was obtained as colorless needles (EtOAc/n-hexanes): mp 272-274° C.; [α]$_D$-10.7 (c. 0.02, CHCl$_3$); IR (film) v$_{max}$ 3426, 1718, 1646, 1242, 1098 cm-1; $_1$H NMR (CDCl$_3$, 600 MHz) and $_{13}$C NMR (CDCl$_3$, 125 MHz), see Table 1; LRESIMS m/z 551 [M+Na]+551 (100), 548, (2.65), 547 (10.60), 546 (14.98), 497 (13.04); HRESIMS m/z [M+Na]+551.2080, (calcd for C$_{25}$H$_{36}$O$_{12}$Na, 551.2104).

Example 20

Synthesis of Compound (26)

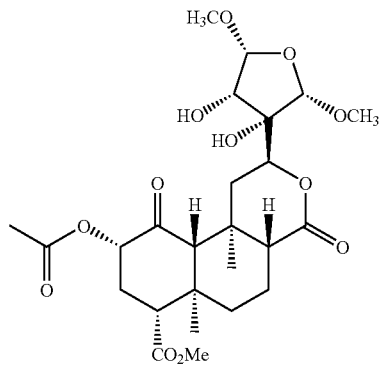

From the chromatography in Example 19 Salvinicin B (26) was obtained as a white solid: mp 151-153° C.; [α]$_D$-26.0 (c. 0.05, CHCl$_3$); IR(film) v$_{max}$ 3426, 1718, 1646, 1242, 1098, cm-1; $_1$H NMR (CDCl$_3$, 600 MHz) and $_{13}$C NMR (CDCl$_3$, 125 MHz); LRESIMS m/z 551 [M+Na]+551 (100), 548, (2.65), 547 (10.60), 546 (14.98), 497 (13.04); HRESIMS m/z [M+Na]+551.2089, (calcd for C$_{25}$H$_{36}$O$_{12}$Na, 551.2104).

Example 21

(2S,4aR,6aR,7R,9S,10aS,10bR)-9-(Acetoxy)-2-(2,5-dimethoxy-2,5-dihydrofuran-3-yl)-dodecahydro-6a, 10b-dimethyl-4,10-dioxo-2H-naphtho[2,1-c]pyran-7-carboxylic acid methyl ester (27)

A solution of bromine (0.075 mL, 1.46 mmol) in MeOH (1 mL) was added in a dropwise manner to a solution of 1 (0.25 g, 0.59 mmol) in a mixture of CH$_2$Cl$_2$ (50 mL) and MeOH (2 mL) at −30° C. The mixture was allowed to stir at −30° C. for 1 h and was quenched by the addition of saturated NaHCO$_3$ (100 mL). The layers were separated and the organic layer was collected, washed with saturated NaHCO$_3$ (50 mL) and H$_2$O (70 mL), and dried (Na$_2$SO$_4$). Removal of the solvent under under reduced pressure afforded a white foam. The foam was purified by flash column chromatography (eluent: EtOAc/n-hexanes, 60%) to give 0.27 g (93%) of 27 as a colorless oil: $^1$H NMR (CDCl$_3$): δ 1.10 (3H, s); 1.40 (3H, s); 1.56 (2H, m); 1.68 (1H, dd, J=2.7, 12.6); 1.78 (1H, dd, J=2.7, 9.9); 2.13 (1H, m); 2.17 (3H, s); 2.17 (1H, s); 2.30 (2H, m); 2.47 (1H, m); 2.75 (1H, dd, J=5.6, 10.9); 3.39 (3H, dd, J=1.4, 2.0); 3.44 (3H, dd); 3.73 (3H, s); 5.14 (2H, m); 5.59 (1H, tt); 5.85 (2H); $^{13}$C NMR (CDCl$_3$): δ 15.7, 16.8, 19.4, 35.5, 36.4, 39.1, 43.4, 44.3, 51.5, 52.2, 54.8, 61.2, 64.7, 72.4, 110.0, 127.5, 128.2, 130.1, 133.5, 141.2, 142.4, 145.1, 171.7, 173.0, 205.3; HRESIMS m/z [M+Na]$^+$551.2080, (calcd for C$_{25}$H$_{36}$O$_{12}$Na, 551.2104).

Example 22

Preparation of Salvinicin A (25) and Salvinicin B (26)

To a solution of 27 (0.27 g, 0.54 mmol) in THF (30 mL) at −10° C. under nitrogen was added with vigorous stirring KMnO$_4$ (0.09 g, 0.54 mmol) in H$_2$O (10 mL). The resulting mixture was stirred at −10° C. for 30 min and was then allowed to warm to room temperature and stirred for a further 16 h. The mixture was filtered and the residue was washed with THF (2×30 mL). The solvent was removed under reduced pressure affording a crude oil. The crude oil was dissolved in EtOAc (50 mL) and the solution was washed with H$_2$O (70 mL) and dried (Na$_2$SO$_4$). Removal of the solvent under reduced pressure afforded a crude mixture. The mixture was subjected to flash chromatography eluting with 50%-70% EtOAc/n-hexanes to afford 25 (0.03 g, 17%), 26 (0.04 g, 27%) and trans-27 (0.11 g). Compounds 25 and 26 showed [α]$_D$, IR, $^1$H NMR, $^{13}$C NMR and MS identical with those previously reported for the natural diterpenoids previously found in *S. divinorum* (See Harding W. W. et al., Org Lett., 2005, 15, 2761-2765).

Example 23

(2S,4aR,6aR,7R,9S,10aS,10bR)-9-(Acetoxy)-dodecahydro-6a,10b-dimethyl-4,10-dioxo-2H-naphtho[2,1-c]pyran-2,7-dicarboxylic acid 7-methyl ester (28)

A solution of 1 (0.10 g, 0.23 mmol), in CCl$_4$/CH$_3$CN/H$_2$O (2:2:3, 7 mL) was stirred at room temperature. To the solution was added NaIO$_4$ (0.75 g, mmol) followed by RuCl$_3$.3H$_2$O (g, mmol). The mixture was stirred vigorously at room temperature for 1 h and then filtered through a pad of celite. The celite pad was washed with EtOAc (50 mL) and the organic layer was collected. The organic layer was washed with saturated NaHCO$_3$ (30 mL) and the aqueous layer was collected. The aqueous layer was then acidified with 2 N HCl (50 mL) and extracted with EtOAc (50 mL). The organic extract was washed with water (2×30 mL), dried (Na$_2$SO$_4$), filtered, and concentrated under reduced pressure to yield 0.70 g (74%) of 28 as a white solid: $^1$H NMR (CDCl$_3$): δ 1.07 (3H, s); 1.37 (3H, s); 1.62 (4H, m); 2.13 (2H, m); 2.19 (1H, s); 2.30 (2H, m); 2.38 (1H, s); 2.59 (1H, dd, J=6.6, 13.5); 2.85 (1H, dd, J=6.0, 11.4); 3.72 (3H, s); 5.01 (1H, dd, J=6.9, 10.2); 5.28 (1H, dd, J=9.3, 10.8); 5.78 (broad); $^{13}$C NMR (acetone-d$_6$): δ 15.7, 16.8, 19.4, 35.5, 36.4, 39.1, 43.4, 44.3, 51.5, 52.2, 54.8, 61.2, 64.7, 72.4, 110.0, 127.5, 128.2, 130.1, 133.5, 141.2, 142.4, 145.1, 171.7, 173.0, 205.3; HRESIMS m/z [M+H]$^+$ 411.1672, (calcd for C$_{20}$H$_{27}$O$_9$, 411.1655).

Example 24

(2S,4aR,6aR,7R,9S,10aS,10bR)-9-(Acetoxy)-2-(2-bromofuran-3-yl)-dodecahydro-6a,10b-dimethyl-4,10-dioxo-2H-naphtho[2,1-c]pyran-7-carboxylic acid methyl ester (29)

A solution of 1 (0.10 g, 0.23 mmol) and N-Bromosuccinimide (0.46 g, 0.25 mmol) in acetonitrile (40 mL) was stirred at room temperature for 2.5 h. Solid Na$_2$CO$_3$ (0.30 g) was added and the mixture stirred at room temperature for 5 minutes. The reaction mixture was filtered to remove solid Na$_2$CO$_3$ and concentrated under reduced pressure. The crude product was purified by flash column chromatography (eluent: n-hexanes/EtOAc, 2:3) in 40% EtOAc:Hexanes to yield 0.45 g (38%) of 29 as a colorless oil: $^1$H NMR (CDCl$_3$): δ 1.14 (3H, s); 1.49 (3H, s); 1.62 (3H, m); 1.82 (1H, dd, J=3.5, 10.6); 2.17 (3H, s); 2.18 (2H, m); 2.31 (2H, m); 2.41 (1H, dd, J=5.1, 13.5); 2.78 (1H, t, J=8.4); 2.78 (1H, s); 3.75 (3H, s); 5.14 (1H, dd, J=9.6, 10.5); 5.45 (1H, dd, J=5.4, 12.0); 6.40 (1H, d, J=2.1); 7.44 (1H, d, J=2.4); $^{13}$C NMR (acetone-d$_6$): δ 15.7, 16.8, 19.4, 35.5, 36.4, 39.1, 43.4, 44.3, 51.5, 52.2, 54.8, 61.2, 64.7, 72.4, 110.0, 127.5, 128.2, 130.1, 133.5, 141.2, 142.4, 145.1, 171.7, 173.0, 205.3; HRESIMS m/z [M+H]$^+$ 511.0947, (calcd for C$_{23}$H$_{28}$O$_8$Br, 511.0968).

Example 25

(2S,4aR,6aR,7R,9S,10aS,10bR)-9-(Acetoxy)-2-(5-bromo-2-oxo-2,5-dihydrofuran-3-yl)-dodecahydro-6a,10b-dimethyl-4,10-dioxo-2H-naphtho[2,1-c]pyran-7-carboxylic acid methyl ester (30)

A solution of 1 (0.10 g, 0.23 mmol) in DMF (40 mL) was cooled to 0° C. in an ice bath. A solution of Br$_2$ in DMF was prepared by dissolving 1 mL of Br$_2$ in 9 mL of DMF. A 0.1 mL portion of this solution was added over 10 min. to the stirring solution of 1 and stirred for 20 minutes. An additional 0.05 mL of the Br$_2$ solution was added over 2 minutes and the reaction was allowed to warm to room temperature and stirred for 1 hour. The mixture was diluted with H$_2$O and extracted with diethyl ether (2×20 mL). The combined organic extracts were then dried (Na$_2$SO$_4$), filtered, and concentrated under reduced pressure to yield a crude oil. The oil was purified by flash column chromatography (eluent: n-hexanes/EtOAc, 1:1) to give 30 as a white solid: $^1$H NMR (CDCl$_3$): δ 1.11 (3H, s); 1.45 (3H, s); 1.64 (m); 1.80 (m); 2.17 (3H, s); 2.31 (2H, m); 2.52 (1H, m); 2.74 (1H, dd, J=5.4, 11.4); 3.73 (3H, s); 5.13 (1H, dd, J=9.0, 11.4); 5.41 (1H, dd, J=5.7, 11.7); 6.86 (1H, dd, J=1.5, 3.9); 7.45 (1H, dt, J=1.5, 5.1); $^{13}$C NMR (acetone-d$_6$): δ 15.7, 16.8, 19.4, 35.5, 36.4, 39.1, 43.4, 44.3, 51.5, 52.2, 54.8, 61.2, 64.7, 72.4, 110.0, 127.5, 128.2, 130.1, 133.5, 141.2, 142.4, 145.1, 171.7, 173.0, 205.3; HRESIMS m/z [M+H]$^+$526.0838, (calcd for C$_{23}$H$_{27}$O$_9$Br,).

Example 26

(2S,4aR,6aR,7R,9S,10aS,10bR)-9-(Imidazole-1-carbothioyloxy)-dodecahydro-6a,10b-dimethyl-4,10-dioxo-2H-naphtho[2,1-c]pyran-7-carboxylic acid methyl ester (31)

A solution of 8a (0.14 g, 0.36 mmol), 1,1'-thiocarbonyldiimidazole (0.19 g, 1.07 mmol), and a catalytic amount of DMAP in $CH_2Cl_2$ (30 mL) was stirred at room temperature for 3 h. The solvent was removed under reduced pressure to yield a crude solid. The solid was purified by flash column chromatography (eluent: n-hexanes/EtOAc, from 50-65% EtOAc) to give 0.12 g (64%) of 31 as a white solid, mp 207-208° C.: $^1$H NMR ($CDCl_3$): δ 1.18 (3H, s); 1.48 (3H, s); 1.66 (3H, m); 1.87 (1H, dd, J=2.5, 10.0); 2.18 (2H, m); 2.30 (1H, s); 2.53 (3H, m); 2.87 (1H, dd, J=3.3, 12.3); 3.76 (3H, s); 5.50 (1H, dd, J=4.3, 10.8); 5.88 (1H, dd, J=7.2, 10.8); 6.39 (1H, dd, J=1.2, 1.8); 7.08 (1H, dd, J=0.6, 1.8); 7.41 (1H, d, J=1.8); 7.44 (1H, t, J=1.8); 7.67 (1H, t, J=1.2); 8.39 (1H, s); $^{13}$C NMR (acetone-$d_6$): δ 15.7, 16.8, 19.4, 35.5, 36.4, 39.1, 43.4, 44.3, 51.5, 52.2, 54.8, 61.2, 64.7, 72.4, 110.0, 127.5, 128.2, 130.1, 133.5, 141.2, 142.4, 145.1, 171.7, 173.0, 205.3; anal. C 59.99%, H 5.64%, O 22.37%, calcd for $C_{28}H_{30}O_8$, C 59.92%, H 5.67%, O 22.25%.

Example 27

(2S,4aR,6aR,7R,9S,10aS,10bR)-Dodecahydro-6a,10b-dimethyl-4,10-dioxo-2H-naphtho[2,1-c]-pyran-7-carboxylic acid methyl ester (32)

A solution of 31 (0.30 g, 0.60 mmol), AIBN (0.02 ml), $Bu_3SnH$ (480 µL1), in toluene (30 mL) was heated at reflux overnight. The reaction mixture was concentrated under reduced pressure to yield a crude solid. The solid was purified by flash column chromatography (eluent: n-hexanes/EtOAc, 10:3) to give 32 as well as 33. $^1$H NMR ($CDCl_3$): δ 1.12 (3H, s); 1.41 (2H, m); 1.59 (3H, s); 1.67 (3H, m); 2.04 (2H, s); 2.12 1H, s); 2.20 (3H, m); 2.35 (1H, m); 2.44 (2H, m); 3.70 (3H, s); 5.54 (1H, dd, J=5.4, 11.7); 6.38 (1H, dd, J=0.6, 1.8); 7.39 (1H, dd, J=1.8, 1.8); 7.43 (1H, dd, J=0.6, 8.7); $^{13}$C NMR (acetone-$d_6$): δ 15.7, 16.8, 19.4, 35.5, 36.4, 39.1, 43.4, 44.3, 51.5, 52.2, 54.8, 61.2, 64.7, 72.4, 110.0, 127.5, 128.2, 130.1, 133.5, 141.2, 142.4, 145.1, 171.7, 173.0, 205.3; HRESIMS m/z [M+H]$^+$375.1805, (calcd for $C_{21}H_{27}O_6$, 375.1808).

Example 28

(2S,4aS,6aR,7R,9S,10aS,10bR)-Dodecahydro-6a,10b-dimethyl-4,10-dioxo-2H-naphtho[2,1-c]-pyran-7-carboxylic acid methyl ester (33)

The title compound was prepared from compound 31 as described in Example 27. $^1$H NMR (acetone-$d_6$): δ 1.09 (3H, s); 1.48 (2H, m); 1.58 (3H, s); 1.84; 1.98 (2H, m); 2.15 (1H, m); 2.19 (1H, s); 2.27 (2H, m); 2.44 (3H, m); 2.67 (1H, dd, J=3.6, 12.6); 3.68 (3H, s); 5.27 (1H, dd, J=0.9, 12.0); 6.38 (1H, dd, J=0.6, 1.8); 7.39 (1H, dd, J=1.8, 1.8); 7.44 (1H, dd, J=0.6, 0.9); $^{13}$C NMR (acetone-$d_6$): δ 15.7, 16.8, 19.4, 35.5, 36.4, 39.1, 43.4, 44.3, 51.5, 52.2, 54.8, 61.2, 64.7, 72.4, 110.0, 127.5, 128.2, 130.1, 133.5, 141.2, 142.4, 145.1, 171.7, 173.0, 205.3; HRESIMS m/z[M+H]$^+$375.1760, (calcd for $C_{21}H_{27}O_6$, 375.1808).

Example 29

(2S,4aR,6aR,7R,9S,10aS,10bR)-9-(Acetoxy)-2-(3-furanyl)-dodecahydro-6a,10b-dimethyl-4,10-dioxo-2H-naphtho[2,1-c]pyran-7-carboxylic acid methyl ester (34)

A mixture of 8a (0.20 g, 0.51 mmol), diphenyl-2-pyridylphosphine (0.20 g, 0.77 mmol) and acetic acid (0.12 mL, 2.05 mmol) was dissolved in anhydrous THF (15 mL) under an argon atmosphere. To this solution was added di-tert-butylazodicarboxylate (DBAD) (0.18 g, 0.77 mmol) in one portion and the mixture was stirred for 18 hours at 60° C. The solvent was removed under reduced pressure and the residue was dissolved in dichloromethane (25 mL). The $CH_2Cl_2$ portion was washed with 4 M HCl (2×25 mL) and saturated NaCl (25 mL), and dried ($Na_2SO_4$). Removal of the solvent under reduced pressure afforded a crude residue. Flash column chromatography (eluent: n-hexanes/EtOAc, 7:3) gave 0.18 g (80%) of 34 as a white crystalline solid, mp 215-216° C.; $^1$H NMR ($CDCl_3$): δ 1.10 (3H, s); 1.28 (1H, dd, J=6.0, 14.1); 1.45 (1H, m); 1.46 (3H, s); 1.64 (2H, m); 1.80 (1H, dd, J=3.0, 9.9); 2.10 (1H, m); 2.13 (3H, s); 2.18 (1H, ddd, J=3.3, 3.3, 15.0); 2.34 (1H, ddd, J=3.3, 13.0, 15.6); 2.45 (1H, dd, J=5.1, 13.5); 2.54 (1H, s); 2.90 (1H, dd, J=3.6, 13.2); 3.71 (3H, s); 4.85 (1H, dd, J=3.2, 3.2); 5.54 (1H, dd, J=5.1, 11.7); 6.38 (1H, dd, J=1.4, 1.7); 7.40 (2H, m); $^{13}$C NMR ($CDCl_3$): δ 15.4, 16.3, 18.3, 21.2, 31.1, 35.2, 38.8, 43.2, 43.6, 51.1, 51.5, 52.1, 61.9, 72.3, 76.6, 108.5, 125.7, 139.4, 143.9, 169.6, 171.4, 172.4, 204.6; anal. C 63.63%, H 6.59%, O 29.70%, calcd for $C_{25}H_{28}N_2O_7S$, C 63.88%, H 6.53%, O 29.60%.

Example 30

(2S,4aR,6aR,7R,9S,10aS,10bR)-9-(Benzoyloxy)-2-(3-furanyl)-dodecahydro-6a,10b-dimethyl-4,10-dioxo-2H-naphtho[2,1-c]pyran-7-carboxylic acid methyl ester (35)

Compound 35 was synthesized using a procedure similar to that described in Example 29 from 8a using benzoic acid to afford 0.19 g (75%) of 35 as a white crystalline solid, mp 223-225° C.; $^1$H NMR ($CDCl_3$): δ 1.13 (3H, s); 1.40 (1H, dd, J=11.6, 13.1); 1.50 (3H, s); 1.64 (2H, m); 1.84 (1H, dd, J=2.9, 11.3); 2.10 (2H, m); 2.37 (1H, ddd, J=3.0, 4.2, 12.3); 2.45 (1H, m); 2.50 (1H, m); 2.62 (1H, s); 3.01 (1H, dd, J=4.4, 12.5); 3.73 (3H, s); 5.00 (1H, dd, J=3.0, 3.0); 5.52 (1H, dd, J=4.7, 11.4); 6.32 (1H, dd, J=0.8, 2.0); 7.32 (1H, m); 7.36 (1H, dd, J=1.8, 1.8); 7.50 (2H, m); 7.65 (1H, tt, J=1.6, 7.5); 8.03 (2H, m); $^{13}$C NMR ($CDCl_3$): δ15.6, 16.2, 18.3, 31.3, 35.2, 38.9, 43.4, 43.6, 51.4, 51.4, 52.1, 61.8, 72.2, 77.5, 108.5, 125.7, 129.0, 129.0, 129.9, 134.1, 139.3, 143.8, 165.4, 171.4, 172.2, 204.8; anal. C 67.85%, H 6.14%, O 25.70%, calcd for $C_{28}H_{30}O_8$, C 68.00%, H 6.11%, O 25.88%.

Example 31

(2S,4aS,6aR,7R,9R,10aS,10bR)-9-(Bromo)-2-(3-furanyl)-dodecahydro-6a,10b-dimethyl-4,10-dioxo-2H-naphtho[2,1-c]pyran-7-carboxylic acid methyl ester (36)

A mixture of salvinorin B (8a) (0.15 g, 0.38 mmol), triphenylphosphine (0.21 g, 0.80 mmol), and bromoform (0.15 g, 0.45 mmol) in CH$_2$Cl$_2$ (30 mL) was stirred at room temperature overnight. TLC indicated that starting material was still present after 16 h, thus additional triphenylphosphine (0.11 g, 0.42 mmol) and bromoform (0.07 g, 0.21 mmol) were added and the mixture was stirred for an additional 3 h. The solvent was removed under reduced pressure affording a crude solid. The oil was purified by column chromatography (eluent: 30% EtOAc/n-hexanes) to afford 0.10 g (59%) of 36 as a white solid, mp 170-173° C. (EtOAc/n-hexanes); $^1$H NMR (CDCl$_3$): δ 1.15 (3H, s); 1.48 (3H, s); 1.60 (3H, m); 1.81 (1H, dd, J=2.7, 9.9); 1.95 (1H, dd, J=13.2, 26.1); 2.1 (2H, m); 2.27 (1H, s); 2.47 (1H, dd, J=4.8, 13.2); 2.66 (1H, m); 2.80 (1H, dd, J=3.3, 13.2); 3.70 (3H, s); 3.89 (2H, d, J=2.4); 4.45 (1H, m); 5.55 (1H, dd, J=4.8, 11.7); 6.38 (1H, dd, J=0.9, 1.5); 7.4 (2H, m).

Example 32

(2S,4aR,6aR,7R,9S,10aS,10bR)-9-(bromo)-2-(3-furanyl)-dodecahydro-6a,10b-dimethyl-4,10-dioxo-2H-naphtho[2,1-c]pyran-7-carboxylic acid methyl ester (37)

A more polar spot was isolated from the chromatography in Example 30 to afford 0.02 g (14%) of 37 as an oil.

Example 33

(2S,4aR,6aR,7R,9S,10aS,10bR)-9-(Azido)-2-(3-furanyl)-dodecahydro-6a,10b-dimethyl-4,10-dioxo-2H-naphtho[2,1-c]pyran-7-carboxylic acid methyl ester (38)

A solution of 36 (0.10 g, 0.22 mmol), sodium azide (0.05 g, 0.77 mmol) and glacial acetic acid in DMF (3 mL) was stirred at room temperature for 4 h. H$_2$O (30 mL) was added and the mixture was extracted with EtOAc (20 mL). The EtOAc solution was washed with H$_2$O (2×20 mL) and saturated NaCl (20 mL) and dried (Na$_2$SO$_4$). Removal of the solvent under reduced pressure afforded a crude solid. The crude solid was purified by column chromatography (eluent: 30% EtOAc/n-hexanes) to afford 0.08 g (86%) of 38 as a white solid, mp 200-203° C. (EtOAc/n-hexanes); $^1$H NMR (CDCl$_3$): δ 1.13 (3H, s); 1.48 (3H, s); 1.68 (5H, m); 2.14 (31H, m); 2.34 (1H, ddd, J=3.6, 7.2, 27); 2.60 (1H, dd, J=5.1, 13.2); 2.72 (1H, dd, J=3.3, 13.2); 3.74 (3H, s); 3.92 (1H, dd, J=7.5, 12.6), 5.56 (1H, dd, J=5.1, 11.7); 6.39 (1H, dd, J=0.9, 1.8); 7.41 (1H, dd, J=1.2, 2.1); 7.43 (1H, dd, J=0.9, 1.5).

Example 34

(2S,4aR,6aR,7R,9S,10aS,10bR)-9-(Amino)-2-(3-furanyl)-dodecahydro-6a,10b-dimethyl-4,10-dioxo-2H-naphtho[2,1-c]pyran-7-carboxylic acid methyl ester (39)

A mixture of 38 (0.08 g, 0.19 mmol), Zn dust (0.16 g, 2.45 mmol) and NH$_4$Cl (g, mmol) in a mixture of CH$_2$Cl$_2$/MeOH (1:4, 20 mL) was stirred at room temperature for 3 h. The mixture was filtered and the filtrate was concentrated to dryness under reduced pressure. 2N NaOH (30 mL) was added to the residue and the mixture was extracted with CH$_2$Cl$_2$ (2×20 mL). The combined CH$_2$Cl$_2$ portion was washed with H$_2$O (30 mL) and dried (Na$_2$SO$_4$). Removal of the solvent under reduced pressure afforded 0.06 g (84%) of 39 as a white solid, mp 237-240° C. (EtOAc/n-hexanes.

Example 35

(2S,4aR,6aR,7R,9S,10aS,10bR)-9-(Acetylamino)-2-(3-furanyl)-dodecahydro-6a,10b-dimethyl-4,10-dioxo-2H-naphtho[2,1-c]pyran-7-carboxylic acid methyl ester (40)

A solution of 39 (0.06 g, 0.16 mmol), acetic anhydride (0.4 mL, 4.23 mmol) and a catalytic amount of DMAP in CH$_2$Cl$_2$ (30 mL) was stirred at room temperature for 2 h. The mixture was washed with 2N HCl (30 mL), 2N NaOH (30 mL), and H$_2$O (30 mL) and dried (Na$_2$SO$_4$). Removal of the solvent under reduced pressure afforded a crude solid. The crude solid was purified by column chromatography (eluent: 4% MeOH/CH$_2$Cl$_2$) to afford 0.04 g (58%) of 40 as a white solid, mp 222-224° C. (EtOAc/n-hexanes).

Example 36

(2S,4aR,6aR,7R,9S,10aS,10bR)-9-(Benzoylamino)-2-(3-furanyl)-dodecahydro-6a,10b-dimethyl-4,10-dioxo-2H-naphtho[2,1-c]pyran-7-carboxylic acid methyl ester (41)

A solution of 39 (0.10 g, 0.26 mmol), benzoyl chloride (0.11 g, 0.78 mmol) and DMAP (0.08 g, 0.78 mmol) in CH$_2$Cl$_2$ (20 mL) was stirred at room temperature for 2 h. Absolute MeOH (15 mL) was added and the solvent was removed under reduced pressure. CH$_2$Cl$_2$ (25 mL) was added to the residue and the solution was washed with 10% HCl (2×20 mL), H$_2$O (3×20 mL), and saturated NaCl (3×20 mL) and dried (Na$_2$SO$_4$). Removal of the solvent under reduced pressure afforded 0.09 g (67%) of 10 as a white crystalline solid, mp 155-157° C. (EtOAc/n-hexanes); $^1$H NMR (CDCl$_3$): δ 1.44 (3H, s); 1.50 (3H, s); 1.63 (3H, m); 1.82 (1H, dd, J=2.1, 10.5); 2.0 (1H, m); 2.12 (1H, dd, J=2.7, 8.4); 2.17 (1H, m); 2.32 (1H, s); 2.48 (1H, dd, J=5.4, 13.2); 2.79 (1H, dd, J=3.3, 6.9); 2.87 (1H, dd, J=2.7, 13.5); 3.71 (3H, s); 4.69 (1H, m); 5.55 (1H, dd, J=5.1, 11.4); 6.37 (1H, dd, J=0.9, 1.8); 7.1 (1H, d, J=6.0); 7.39 (1H, t, J=1.8); 7.41 (1H, dd, J=0.9, 1.8); 7.46 (1H, m); 7.53 (1H, tt, J=1.5, 2.7, 7.2); 7.80 (1H, t, J=2.4); 7.82 (1H, t, J=1.2.

Example 37

(2S,4aR,6aR,7R,9S,10aS,10bR)-9-(Methanesulfonylamino)-2-(3-furanyl)-dodecahydro-6a,10b-dimethyl-4,10-dioxo-2H-naphtho[2,1-c]pyran-7-carboxylic acid methyl ester (42)

A solution of 39 (0.10 g, 0.26 mmol), methanesulfonyl chloride (0.08 mL, 1.03 mmol), NEt$_3$ (0.04 mL, 0.28 mmol) and a catalytic amount of DMAP in CH$_2$Cl$_2$ (50 mL) was stirred at room temperature for 2 h. The mixture was washed with 2N HCl (30 mL), 2N NaOH (30 mL), and H$_2$O (30 mL) and dried (Na$_2$SO$_4$). Removal of the solvent under reduced pressure afforded a crude solid. The crude solid was purified by column chromatography (eluent: 2% MeOH/CH$_2$Cl$_2$) to afford 0.7 g (56%) of 42 as a white crystalline solid, mp 262-265° C. (EtOAc/n-hexanes); $^1$H NMR (CDCl$_3$): δ 1.09 (3H, s); 1.46 (3H, s); 1.60 (3H, m); 1.79 (1H, dd, J=2.7, 9.6); 2.07 (2H, m); 2.18 (1H, m); 2.21 (1H, s); 2.50 (2H, m); 2.75 (1H, dd, J=3.6, 13.2); 2.99 (3H, s); 3.72 (3H, s); 4.15 (1H, m);

5.34 (1H, d, J=5.4); 5.55 (1H, dd, J=5.1, 11.4); 6.38 (1H, dd, J=0.9, 1.2); 7.41 (1H, dd, J=1.5, 1.8); 7.43 (1H, dd, J=0.9, 1.5).

Example 38

(2S,4aR,6aR,7R,9S,10aS,10bR)-9-(Benzenesulfonylamino)-2-(3-furanyl)-dodecahydro-6a,10b-dimethyl-4,10-dioxo-2H-naphtho[2,1-c]pyran-7-carboxylic acid methyl ester (43)

A solution of 39 (0.08 g, 0.21 mmol), benzenesulfonyl chloride (0.07 g, 0.42 mmol), triethylamine (0.06 g, 0.63 mmol), and a catalytic amount of DMAP in $CH_2Cl_2$ (40 mL) was stirred at room temperature for 18 h. Absolute MeOH was then added and the solution was washed with 10% HCl (3×25 mL) and saturated NaCl (2×25 mL), dried ($Na_2SO_4$), filtered, and concentrated under reduced pressure to yield a crude solid. The solid was purified by flash column chromatography (eluent: n-hexanes/EtOAc, 1:1). Removal of the solvent under reduced pressure gave 0.11 g (97%) of 43 as a white solid, mp 271-273° C. (EtOAc/n-hexanes): $^1$H NMR (acetone-$d_6$): δ 0.98 (3H, s); 1.29 (3H, s); 1.52 (2H, m); 1.65 (1H, m); 1.70 (1H, ddd, J=3.0, 3.0, 12.6); 1.82 (1H, ddd, J=1.8, 5.1, 13.5); 1.95 (1H, ddd, J=6.3, 6.3, 10.2); 2.09 (1H, d, J=13.2); 2.22 (1H, dd, J=2.7, 11.7); 2.29 (1H, ddd, J=3.3, 6.9, 13.5); 2.62 (1H, s); 2.96 (1H, dd, J=3.5, 13.4); 3.66 (3H, s); 4.19 (1H, m); 5.47 (1H, dd, J=5.4, 12.0); 6.53 (1H, dd, J=0.9, 1.5); 6.69 (1H, d, J=8.4); 7.38 (1H, m); 7.40 (1H, d, J=6.9); 7.44 (1H, dd, J=2.1, 3.0); 7.60 (2H, m); 7.80 (2H, m); $^{13}$C NMR (acetone-$d_6$): δ 15.7, 16.8, 19.4, 35.5, 36.4, 39.1, 43.4, 44.3, 51.5, 52.2, 54.8, 61.2, 64.7, 72.4, 110.0, 127.5, 128.2, 130.1, 133.5, 141.2, 142.4, 145.1, 171.7, 173.0, 205.3.

Example 39

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution | q.s. |
| (pH adjustment to 7.0-7.5) | |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution | q.s. |
| (pH adjustment to 7.0-7.5) | |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

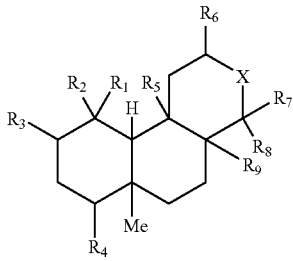

wherein:
- $R_1$ is H, $(C_1\text{-}C_6)$alkyl, $(C_1\text{-}C_6)$alkoxy, or $(C_1\text{-}C_6)$alkanoyloxy and $R_2$ is H or $(C_1\text{-}C_6)$alkyl; or $R_1$ and $R_2$ taken together are oxo (=O), thioxo (=S), or $NR_a$;
- $R_3$ is H, halo, azido, hydroxy, $(C_1\text{-}C_6)$alkyl, $(C_1\text{-}C_6)$alkoxy, $(C_1\text{-}C_6)$alkylthio, $(C_1\text{-}C_6)$alkoxy$(C_1\text{-}C_6)$alkoxy, aryl, heteroaryl, aryloxy, heteroaryloxy, aryl$(C_1\text{-}C_6)$alkyl, aryl$(C_1\text{-}C_6)$alkoxy, heteroaryl$(C_1\text{-}C_6)$alkyl, heteroaryl$(C_1\text{-}C_6)$alkoxy, formyloxy, acetoxy, $R_cC(=O)O-$, $R_cC(=S)O-$, $R_cC(=O)S-$, $(R_g)_3SiO-$, $R_dR_eNC(=O)O-$, $(R_h)_3C(=NR_d)O-$, $R_mR_nN-$, or $R_bS(=O)_2O-$;
- $R_4$ is H, hydroxymethyl, $(C_1\text{-}C_6)$alkyl, $(C_1\text{-}C_6)$alkoxymethyl, carboxy, $(C_1\text{-}C_6)$alkoxycarbonyl, or $R_dR_eNC(=O)-$;
- $R_5$ is H or $(C_1\text{-}C_6)$alkyl;
- $R_6$ is $(C_1\text{-}C_6)$alkyl, $(C_1\text{-}C_6)$cycloalkyl, aryl, carboxy, $R_jR_kNC(=O)-$, 3,4-dihydroxy-2,5-dimethoxytetrahydrofuran-3-yl, 2,5-dihydro-2,5-dimethoxyfuran-3-yl, ,2,5-dihydro-5-bromo-2-oxofuran-3-yl, 2,5-dimethoxytetrahydrofuran-3-yl, or heteroaryl;
- $R_7$ and $R_8$ taken together are oxo (=O), thioxo (=S), or $NR_a$;
- $R_9$ is H or $(C_1\text{-}C_6)$alkyl;
- X is —O—, —S—, or $—NR_a—$;
- each $R_a$ is independently H, $(C_1\text{-}C_6)$alkyl, aryl, heteroaryl, aryl$(C_1\text{-}C_6)$alkyl, or heteroaryl$(C_1\text{-}C_6)$alkyl;
- each $R_b$ is independently H, $(C_1\text{-}C_6)$alkyl, $(C_2\text{-}C_6)$alkenyl, aryl, heteroaryl, aryl$(C_1\text{-}C_6)$alkyl, or heteroaryl$(C_1\text{-}C_6)$alkyl;
- each $R_c$ is independently H, $(C_2\text{-}C_6)$alkyl, $(C_2\text{-}C_6)$alkenyl, $(C_2\text{-}C_6)$alkoxycarbonyl, aryl, heteroaryl, aryl$(C_1\text{-}C_6)$alkyl, or heteroaryl$(C_1\text{-}C_6)$alkyl;
- each $R_d$ and $R_e$ is independently H, $(C_1\text{-}C_6)$alkyl, $(C_1\text{-}C_6)$alkenyl, aryl, heteroaryl, aryl$(C_1\text{-}C_6)$alkyl, or heteroaryl$(C_1\text{-}C_6)$alkyl;
- each $R_g$ is independently $(C_1\text{-}C_6)$alkyl;
- each $R_h$ is independently H, $(C_1\text{-}C_6)$alkyl, fluoro, or chloro;
- each $R_j$ and $R_k$ is independently H, $(C_1\text{-}C_6)$alkyl, $(C_1\text{-}C_6)$alkenyl, aryl, heteroaryl, aryl$(C_1\text{-}C_6)$alkyl, or heteroaryl$(C_1\text{-}C_6)$alkyl;
- each $R_m$ and $R_n$ is independently H, $(C_1\text{-}C_6)$alkyl, $(C_1\text{-}C_6)$alkenyl, aryl, heteroaryl, aryloxy, heteroaryloxy, aryl$(C_1\text{-}C_6)$alkyl, aryl$(C_1\text{-}C_6)$alkoxy, heteroaryl$(C_1\text{-}C_6)$alkyl, heteroaryl$(C_1\text{-}C_6)$alkoxy, $(C_1\text{-}C_6)$alkanoyloxy, $R_pC(=O)-$, $R_dR_eNC(=O)-$, $(R_h)_3C(=NR_d)-$, or $R_bS(=O)_2-$;
- each $R_p$ is independently H, $(C_1\text{-}C_6)$alkyl, $(C_2\text{-}C_6)$alkenyl, aryl, heteroaryl, aryl$(C_1\text{-}C_6)$alkyl, or heteroaryl$(C_1\text{-}C_6)$alkyl; and
- each $R_q$ is independently H, $(C_1\text{-}C_6)$alkyl, $(C_2\text{-}C_6)$alkenyl, aryl, heteroaryl, aryl$(C_1\text{-}C_6)$alkyl, or heteroaryl$(C_1\text{-}C_6)$alkyl;
- wherein each aryl is independently a phenyl radical or an ortho-fused bicyclic carbocyclic radical having about nine to ten ring atoms in which at least one ring is aromatic;
- wherein each heteroaryl is thiophene, furan, pyrrole, oxazole, thiazole, imidazole or pyridine;
- wherein any aryl or heteroaryl of $R_3$, $R_6$, and $R_a$-$R_e$, and $R_j$-$R_q$ is optionally substituted with one or more halo, hydroxy, $(C_1\text{-}C_6)$alkyl, $(C_1\text{-}C_6)$alkoxy, $(C_1\text{-}C_6)$alkanoyloxy, $(C_1\text{-}C_6)$alkoxycarbonyl, cyano, nitro, trifluomethyl, trifluoromethoxy, $R_tS(=O)_2—$, or $R_uR_vN$; wherein $R_u$ and $R_v$ are each independently H or $(C_1\text{-}C_6)$alkyl;
- each $R_t$ is independently H, $(C_1\text{-}C_6)$alkyl, $(C_2\text{-}C_6)$alkenyl, aryl, heteroaryl, aryl$(C_1\text{-}C_6)$alkyl, or heteroaryl$(C_1\text{-}C_6)$alkyl; and
- wherein any aryl or heteroaryl of $R_t$ is optionally substituted with one or more halo, hydroxy, $(C_1\text{-}C_6)$alkyl, $(C_1\text{-}C_6)$alkoxy, $(C_1\text{-}C_6)$alkanoyloxy, $(C_1\text{-}C_6)$alkoxycarbonyl, cyano, nitro, trifluomethyl, trifluoromethoxy, or $R_uR_vN$; wherein $R_u$ and $R_v$ are each independently H or $(C_1\text{-}C_6)$alkyl;
- or a pharmaceutically acceptable salt thereof;
- provided that the compound is not a compound of formula (IV):

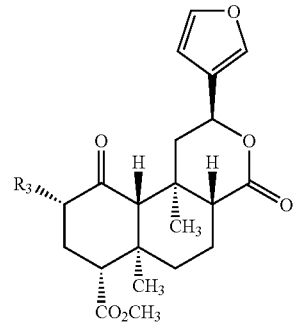

wherein $R_3$ is acetoxy, propanoyloxy, 4-bromobenzoyloxy, 1-naphthylcarbonyloxy, heptanoyloxy, pivaloyloxy, or hydroxy.

2. The compound of claim 1 wherein $R_1$ and $R_2$ taken together are oxo (=O).

3. The compound of claim 1 wherein $R_3$ is propanoyloxy, isobutanoyloxy, methacryloyloxy, methoxyoxalyloxy, benzoyloxy, trimethylsilyloxy, imidazole-1-ylthiocarbonyloxy, methoxymethoxy, aminocarbonyloxy, butanoyloxy, pentanoyloxy, 1-bromobenzoyloxy, 2-bromobenzoyloxy, 3-bromobenzoyloxy, 4-methoxybenzoyloxy, 4-nitrobenzoyloxy, phenylsulfonyloxy, 4-methylphenylsulfonyloxy, 4-methoxyphenylsulfonyloxy, 4-bromophenylsulfonyloxy, (3-pyridylcarbonyloxy, methylsulfonyloxy, hydroxy, 1-imino-2,2,2-trichloroethoxy, phenylaminocarbonyloxy, allylaminocarbonyloxy, 3,4-dichlorobenzoyloxy, bromo, azido, amino, acetylamino, phenylcarbonylamino, methylsulfonylamino, phenylsulfonylamino, or benzoyloxy.

4. The compound of claim 1 wherein $R_3$ is propanoyloxy, methylsulfonyloxy, or benzoyloxy.

5. The compound of claim 1 wherein $R_4$ is carboxy, $(C_1\text{-}C_6)$alkoxycarbonyl or $R_dR_eNC(=O)—$.

6. The compound of claim 1 wherein $R_6$ is phenyl, thienyl, furanyl, pyrrolyl, or pyridyl, optionally substituted with one or more halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluomethyl, trifluoromethoxy, or $R_eR_fN$.

7. The compound of claim 1 wherein $R_6$ is 3-furyl.

8. The compound of claim 1 wherein $R_7$ and $R_8$ taken together are oxo.

9. The compound of claim 1 wherein X is —O—.

10. The compound of claim 1 which is a compound of formula (II):

wherein $R_3$, $R_4$, and $R_6$ have any of the values defined in claim 1; or a pharmaceutically acceptable salt thereof.

11. The compound of claim 1 which is a compound of formula (III):

wherein $R_3$ and $R_4$ have any of the values defined in claim 1; or a pharmaceutically acceptable salt thereof.

12. The compound of claim 11 wherein $R_3$ is benzoyloxy; or a pharmaceutically acceptable salt thereof.

13. The compound of claim 11 wherein $R_3$ is methylsulfonyloxy; or a pharmaceutically acceptable salt thereof.

14. The compound of claim 1 which is a compound of formula IV wherein $R_3$ is aryl, heteroaryl, aryloxy, heteroaryloxy, aryl$(C_1-C_6)$alkyl, aryl$(C_1-C_6)$alkoxy, heteroaryl$(C_1-C_6)$alkyl, heteroaryl$(C_1-C_6)$alkoxy, $R_cC(=O)O-$, $R_dR_eNC(=O)O-$, or $R_bS(=O)_2O-$; each $R_b$ is independently aryl, heteroaryl, aryl$(C_1-C_6)$alkyl, or heteroaryl$(C_1-C_6)$alkyl; each $R_c$ is independently aryl, heteroaryl, aryl$(C_1-C_6)$alkyl, or heteroaryl$(C_1-C_6)$alkyl; $R_d$ is aryl, heteroaryl, aryl$(C_1-C_6)$alkyl, or heteroaryl$(C_1-C_6)$alkyl; and $R_e$ is independently H, $(C_1-C_6)$alkyl, $(C_1-C_6)$alkenyl, aryl, heteroaryl, aryl$(C_1-C_6)$alkyl, or heteroaryl$(C_1-C_6)$alkyl; wherein any aryl or heteroaryl of $R_3$, or $R_b-R_e$ is optionally substituted with one or more halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluomethyl, trifluoromethoxy, or $R_eR_fN$; wherein $R_e$ and $R_f$ are each independently H or $(C_1-C_6)$alkyl; or a pharmaceutically acceptable salt thereof.

15. The compound of claim 14 wherein $R_3$ is benzoyloxy, 3-pyridylcarbonyloxy, or phenylaminocarbonyloxy.

16. A pharmaceutical composition comprising a compound as described in claim 1 and a pharmaceutically acceptable diluent or carrier.

17. A pharmaceutical composition comprising a compound of formula I:

wherein:
$R_1$ is H, hydroxy, $(C_1-C_6)$alkyl, $(C_1-C_6)$alkoxy, or $(C_1-C_6)$alkanoyloxy and $R_2$ is H or $(C_1-C_6)$alkyl; or $R_1$ and $R_2$ taken together are oxo (=O), thioxo (=S), or =$NR_a$;

$R_3$ is H, hydroxy, $(C_1-C_6)$alkyl, $(C_1-C_6)$alkoxy, aryl, heteroaryl, aryloxy, heteroaryloxy, aryl$(C_1-C_6)$alkyl, aryl$(C_1-C_6)$alkoxy, heteroaryl$(C_1-C_6)$alkyl, heteroaryl$(C_1-C_6)$alkoxy, formyloxy, acetoxy, $R_cC(=O)O-$, $(R_g)_3SiO-$, $R_dR_eNC(=O)O-$, $(R_h)_3C(=NR_d)O-$, or $R_bS(=O)_2O-$;

$R_4$ is H, hydroxymethyl, $(C_1-C_6)$alkyl, $(C_1-C_6)$alkoxymethyl, carboxy, $(C_1-C_6)$alkoxycarbonyl; or $R_dR_eNC(=O)-$;

$R_5$ is H or $(C_1-C_6)$alkyl;

$R_6$ is $(C_1-C_6)$alkyl, $(C_1-C_6)$cycloalkyl, aryl, or heteroaryl;

$R_7$ and $R_8$ taken together are oxo (=O), thioxo (=S), or =$NR_a$;

$R_9$ is H or $(C_1-C_6)$alkyl;

X is —O—, —S—, or $NR_a-$;

each $R_a$ is independently H, $(C_1-C_6)$alkyl, aryl, heteroaryl, aryl$(C_1-C_6)$alkyl, or heteroaryl$(C_1-C_6)$alkyl;

each $R_b$ is independently H, $(C_1-C_6)$alkyl, $(C_2-C_6)$alkenyl, aryl, heteroaryl, aryl$(C_1-C_6)$alkyl, or heteroaryl$(C_1-C_6)$alkyl;

each $R_c$ is independently H, $(C_2-C_6)$alkyl, $(C_2-C_6)$alkenyl, $(C_2-C_6)$alkoxycarbonyl, aryl, heteroaryl, aryl$(C_1-C_6)$alkyl, or heteroaryl$(C_1-C_6)$alkyl;

each $R_d$ and $R_e$ is independently H, $(C_1-C_6)$alkyl, $(C_1-C_6)$alkenyl, aryl, heteroaryl, aryl$(C_1-C_6)$alkyl, or heteroaryl$(C_1-C_6)$alkyl;

each $R_g$ is independently $(C_1-C_6)$alkyl; and each $R_h$ is independently H, $(C_1-C_6)$alkyl, fluoro, or chloro;

wherein any aryl or heteroaryl of $R_3$, $R_6$, or $R_a-R_e$ is optionally substituted with one or more halo, hydroxy, $(C_1-C_6)$alkyl, $(C_1-C_6)$alkoxy, $(C_1-C_6)$alkanoyloxy, $(C_1-C_6)$alkoxycarbonyl, cyano, nitro, trifluomethyl, trifluoromethoxy, or $R_eR_fN$; wherein $R_e$ and $R_f$ are each independently H or $(C_1-C_6)$alkyl;

or a pharmaceutically acceptable salt thereof;

and a pharmaceutically acceptable diluent or carrier provided that the compound is not a compound of formula (IV):

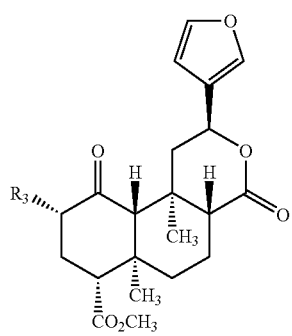

wherein R₃ acetoxy, propanoyloxy, or heptanoyloxy.

18. A therapeutic method for treating pain, drug addiction, or alcohol addiction comprising administering to a mammal, an effective amount of a compound of formula (IV):

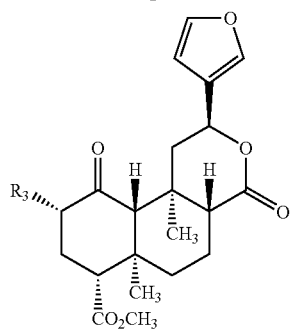

wherein R₃ is beuzoyloxy; or a pharmaceutically acceptable salt thereof.

19. A pharmaceutical composition comprising a compound of formula (IV):

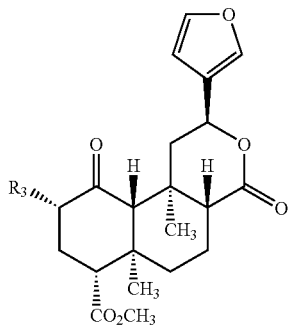

wherein R₃ is 4-bromobenzoyloxy, or a pharmaceutically acceptable salt thereof, and a pharmaceutically acceptable diluent or carrier.

* * * * *

UNITED STATES PATENT AND TRADEMARK OFFICE
CERTIFICATE OF CORRECTION

PATENT NO. : 7,728,001 B2
APPLICATION NO. : 11/224706
DATED : June 1, 2010
INVENTOR(S) : Thomas Prisinzano and Richard Brian Rothman It is certified that error appears in the above-identified patent and that said Letters Patent is hereby corrected as shown below:

On the Title Pg,
Page 1, Item (56), line 10, delete "Receptor.Ligands" and replace with --Receptor Ligands--.

Page 2, Item (56), lines 12-13, insert --" "-- around the title, so it appears as follows:
"A facile method for the preparation of deuterium labeled salvinorin A: synthesis of [2,2,2-$^2$H$_3$]-salvinorin A", Page 2, Item (56), lines 3-5, insert --" "-- around the title, so it appears as follows:
"Divinorin A, a Psychotropic Terpenoid, and Divinorin B from the Hallucinogenic Mexican Mint *Salvia divinorum*", Page 2, Item (56), lines 6-7, insert --" "-- around the title, so it appears as follows:
"Studies toward the Pharmacophore of Salvinorin A, a Potent k Opioid Receptor Agonist", Claim 1, column 35, line 20, insert a double bond before "NR$_a$;", so it appears as follows:

=NR$_a$;

Claim 1, column 35, line 36, delete the first "," in the phrase ",2,5-dihydro-5-bromo-2-oxofuran-3-yl," so it appears as follows:

2,5-dihydro-5-bromo-2-oxofuran-3-yl,

Claim 18, column 40, line 1, delete "beuzoyloxy;" and replace with --benzoyloxy;--.

Signed and Sealed this
Twelfth Day of April, 2011

David J. Kappos
*Director of the United States Patent and Trademark Office*